US009827299B2

(12) United States Patent
Malley et al.

(10) Patent No.: US 9,827,299 B2
(45) Date of Patent: Nov. 28, 2017

(54) SELECTIVELY DISRUPTED WHOLE-CELL VACCINE

(75) Inventors: Richard Malley, Beverly, MA (US); Porter Anderson, Key Largo, FL (US); Yingjie Lu, West Roxbury, MA (US); George A. Robertson, Fairfax Station, VA (US); Mark Alderson, Bainbridge Island, WA (US); Jean-Francois Lucien Maisonneuve, Federal Way, WA (US); Andrea Maria Tate, Issaquah, WA (US); Waldely de Oliveira Dias, Sao Paulo (BR); Viviane Maimoni Gonçalves, Sao Paulo (BR)

(73) Assignees: Children's Medical Center Corporation, Boston, MA (US); Path Vaccine Solutions, Seattle, WA (US); Fundacao Butantan, Sao Paulo (BR)

( * ) Notice: Subject to any disclaimer, the term of this patent is extended or adjusted under 35 U.S.C. 154(b) by 0 days.

(21) Appl. No.: 13/500,925

(22) PCT Filed: Oct. 12, 2010

(86) PCT No.: PCT/US2010/052298
§ 371 (c)(1),
(2), (4) Date: Jun. 22, 2012

(87) PCT Pub. No.: WO2011/044576
PCT Pub. Date: Apr. 14, 2011

(65) Prior Publication Data
US 2012/0251577 A1    Oct. 4, 2012

Related U.S. Application Data

(60) Provisional application No. 61/250,348, filed on Oct. 9, 2009, provisional application No. 61/380,429, filed on Sep. 7, 2010.

(51) Int. Cl.
*C12Q 1/00* (2006.01)
*A61K 39/09* (2006.01)
*A61K 39/00* (2006.01)

(52) U.S. Cl.
CPC ...... *A61K 39/092* (2013.01); *A61K 2039/521* (2013.01); *A61K 2039/543* (2013.01); *A61K 2039/55505* (2013.01); *A61K 2039/55544* (2013.01)

(58) Field of Classification Search
CPC .............................. A61K 39/92; A61K 39/092
USPC ..................................................... 424/244.1
See application file for complete search history.

(56) References Cited

U.S. PATENT DOCUMENTS

| | | | | |
|---|---|---|---|---|
| 3,501,776 A | * | 3/1970 | Beeker ...................... | A61F 2/58 623/25 |
| 3,755,557 A | * | 8/1973 | Jacobs ................ | A61K 39/095 424/202.1 |
| 3,852,420 A | * | 12/1974 | Usdin ....................... | 424/244.1 |
| 3,920,811 A | * | 11/1975 | Lund .......................... | 424/280.1 |
| 4,675,176 A | | 6/1987 | Gerber | |
| 5,075,223 A | * | 12/1991 | Lubitz et al. ................ | 435/69.1 |
| 5,281,392 A | * | 1/1994 | Rubinstein ............. | A61K 33/14 422/28 |
| 5,418,130 A | | 5/1995 | Platz et al. | |
| 5,837,250 A | * | 11/1998 | Kandil et al. .............. | 424/193.1 |
| 5,958,414 A | | 9/1999 | Regnery et al. | |
| 6,022,728 A | * | 2/2000 | Mulks et al. .............. | 435/252.1 |
| 6,042,838 A | | 3/2000 | Briles et al. | |
| 6,132,709 A | | 10/2000 | Berg | |
| 6,258,355 B1 | * | 7/2001 | Cavaliere widow Vesely et al. ......................... | 424/93.45 |
| 6,287,555 B1 | * | 9/2001 | Gill et al. .................... | 424/93.1 |
| 6,378,677 B1 | * | 4/2002 | Kuroda et al. .............. | 192/35 |
| 6,416,959 B1 | * | 7/2002 | Giuliano et al. ............. | 435/7.2 |
| 6,743,430 B1 | * | 6/2004 | Parizek et al. ............. | 424/203.1 |
| 6,777,202 B2 | * | 8/2004 | Lubitz et al. ................ | 435/69.1 |
| 6,896,887 B2 | * | 5/2005 | Leenhouts et al. ........ | 424/234.1 |
| 7,067,639 B2 | * | 6/2006 | Leenhouts et al. ........... | 530/412 |
| 7,172,762 B1 | | 2/2007 | Roberts et al. | |
| 7,291,276 B1 | * | 11/2007 | Zahn ........................ | C02F 1/50 210/759 |
| 7,399,476 B2 | | 7/2008 | Lubitz et al. | |
| 7,429,389 B2 | | 9/2008 | Leonard et al. | |
| 7,462,359 B2 | | 12/2008 | Choromanski et al. | |
| 8,609,107 B2 | * | 12/2013 | Doucette-Stamm et al. ......................... | 424/190.1 |
| 8,628,766 B2 | * | 1/2014 | Klaasen et al. ............ | 424/93.44 |

(Continued)

FOREIGN PATENT DOCUMENTS

| | | | | |
|---|---|---|---|---|
| FR | 2174745 | * | 10/1973 | ............. A61K 23/00 |
| WO | 90/11087 | * | 10/1990 | ............. A61K 39/02 |

(Continued)

OTHER PUBLICATIONS

Malley, Richard et al, Infection and Immunity, vol. 72(7), pp. 4290-4292 Jul. 2004.*

(Continued)

*Primary Examiner* — Albert Navarro
(74) *Attorney, Agent, or Firm* — Nixon Peabody LLP

(57) ABSTRACT

The present invention provides for immunogenic compositions and methods for producing an immunogenic composition with multiple immunity-inducing fractions of killed, whole-cell *Streptococcus pneumoniae* by selectively disrupting a whole cell bacterial preparation in such a manner that a soluble fraction that induces a primarily antibody response, and a cellular fraction that induces a primarily antibody-independent response, remain in the immunogenic composition.

4 Claims, 34 Drawing Sheets

(56) References Cited

U.S. PATENT DOCUMENTS

| | | | |
|---|---|---|---|
| 8,668,911 B2* | 3/2014 | Baker et al. | 424/236.1 |
| 2003/0003511 A1* | 1/2003 | Lubitz et al. | 435/7.1 |
| 2003/0180816 A1* | 9/2003 | Leenhouts et al. | 435/7.22 |
| 2003/0186851 A1* | 10/2003 | Leenhouts et al. | 514/8 |
| 2004/0141986 A1* | 7/2004 | Parizek et al. | 424/184.1 |
| 2005/0208077 A1* | 9/2005 | Evans et al. | 424/244.1 |
| 2005/0222057 A1* | 10/2005 | Brahmbhatt et al. | 514/44 |
| 2006/0003454 A1* | 1/2006 | Suzuki et al. | 435/471 |
| 2006/0121058 A1* | 6/2006 | Malley et al. | 424/244.1 |
| 2006/0275328 A1* | 12/2006 | Kitahara et al. | 424/244.1 |
| 2007/0092491 A1* | 4/2007 | Sattar et al. | 424/93.4 |
| 2008/0181949 A1* | 7/2008 | Baker et al. | 424/484 |
| 2008/0254058 A1* | 10/2008 | Glenting et al. | 424/197.11 |
| 2009/0214596 A1* | 8/2009 | Seino | A61K 9/0043 424/275.1 |
| 2009/0263414 A1* | 10/2009 | Leenhouts et al. | 424/194.1 |
| 2009/0285821 A1* | 11/2009 | Joens et al. | 424/139.1 |
| 2010/0196410 A1* | 8/2010 | Choi et al. | 424/190.1 |
| 2010/0203139 A1* | 8/2010 | Baker et al. | 424/484 |
| 2010/0272776 A1* | 10/2010 | Harlow et al. | 424/423 |
| 2011/0129494 A1* | 6/2011 | Detraz et al. | 424/204.1 |
| 2011/0143362 A1* | 6/2011 | Oyler et al. | 435/6.18 |
| 2011/0172826 A1* | 7/2011 | Amodei et al. | 700/266 |
| 2012/0021003 A1* | 1/2012 | Klaasen et al. | 424/244.1 |
| 2013/0004525 A1* | 1/2013 | Slifka et al. | 424/184.1 |
| 2014/0193461 A1* | 7/2014 | Baker et al. | 424/244.1 |

FOREIGN PATENT DOCUMENTS

| | | | | |
|---|---|---|---|---|
| WO | 91/04742 | * | 4/1991 | A61K 35/74 |
| WO | 1993/21951 | | 11/1993 | |
| WO | 2006/017895 | | 2/2006 | |
| WO | 2006/127020 | * | 11/2006 | C07K 14/315 |
| WO | 2007/052163 | | 5/2007 | |
| WO | 2009/013443 | * | 1/2009 | A61K 39/085 |

OTHER PUBLICATIONS

Malley, Richard et al, Infection and Immunity, vol. 69(8), pp. 4870-4873, Aug. 2001.*

Verdu, EF et al, Clin. Exp. Immunol., 2000, vol. 120, pp. 46-50, Oral administration of antigens from intestinal flora anaerobic bacteria reduces the severity of experimental acute colitis in Balb/c mice.*

Gilbert, Christophe et al, Infection and Immunity, vol. 68(6), pp. 3251-3260.*

Wirawan, Ruth E. et al, Microbiology, vol. 153, 2007, pp. 1619-1630.*

Srivastava, SK et al, Studies on the immunogenicity of *Streptococcus equi* Vaccines in Foals, Can. J. Comp. Med., 1985, vol. 49, pp. 351-356.*

Rains, ATH et al, 1956, Lancet, vol. 271, p. 830-832, Mangaement of an artery-graft bank.*

Himmelfarb, P et al, An Evaluation of B-propiolactone for Sterilization of Fermentation Media, Appl. Microbiology, vol. 9, pp. 534-537.*

Goldblum et al, (1992), Infection and Immunity, Jul. 1982, vol. 37(1), pp. 336-343, Gram Positive Bacteria Induced Granulocytopenia and Pulmonary Leukostasis in Rabbits.*

Arandjus, C et al, Respiratory Medicine, 2006, vol. 100, pp. 1671-1681, Oral Bacterial vaccines for the prevention of acute exacerbations in chronic obstructive pulmonary disease and chronic bronchitis.*

Mehta, S et al, Anaesthesia, May 1974, vol. 29(3), pp. 280-289.*

Chen et al., J Immunol, 177:6044-6051 (2006). "Endogenous IL-1R1 signaling is critical for cognate CD4+ T cell help for induction in vivo type 1 and type 2 antipolysaccharide and antiprotein Ig isotype responses to intact *Streptococcus pneumoniae*, but not to a soluble pneumococcal conjugate vaccine."

Kamaraj et al., Res Vet Sci, 85:589-94 (2008). "Inactivated infections bovine rinotraceitis virus in BPL. BPL destroys the nucleic acid core of viruses but does not damage the capsid."

Lu et al., Clinical and Vaccine Immunology, 17(6):1005-1012 (2010). "Options for inactivation, adjuvant, and route of topical administration of a killed, unencapsulated, pneumococcal whole-cell vaccine."

Becker et al., Virus Genes, 8(3):199-214 (1994). "Need for cellular and humoral immune responses in bovines to ensure protection from foot-and-mouth disease virus (FMDV)—a point of view."

Healey et al., Infect Immun, 73(9):5945-5951 (2005). "Humoral and cell-mediated adaptive immune responses are required for protection against Burkholderia pseudomallei challenge and bacterial clearance post infection."

Snapper et al., Curr Protein Pept Sci, 7(4):295-305 (2006). "Differential regulation of protein- and polysaccharide-specific Ig isotype production in vivo in response to intact *Streptococcus pneumoniae*."

Walker, Vaccine, 23(26):3369-3385 (2005). "Consideration for development of whole cell bacterial vaccines to prevent diarrheal diseases in children in developing countries."

Braido et al., "Bacterial lysate in the prevention of acute exacerbation of COPD and in respiratory recurrent infections" International Journal of COPD 2(3):335-345 (2007).

Lanzilli et al., "In vivo effect of immunostimulating bacterial lysate on human B lymphocytes" International Journal of Immunopathology and Pharmacology 19(3):551-559 (2006).

* cited by examiner

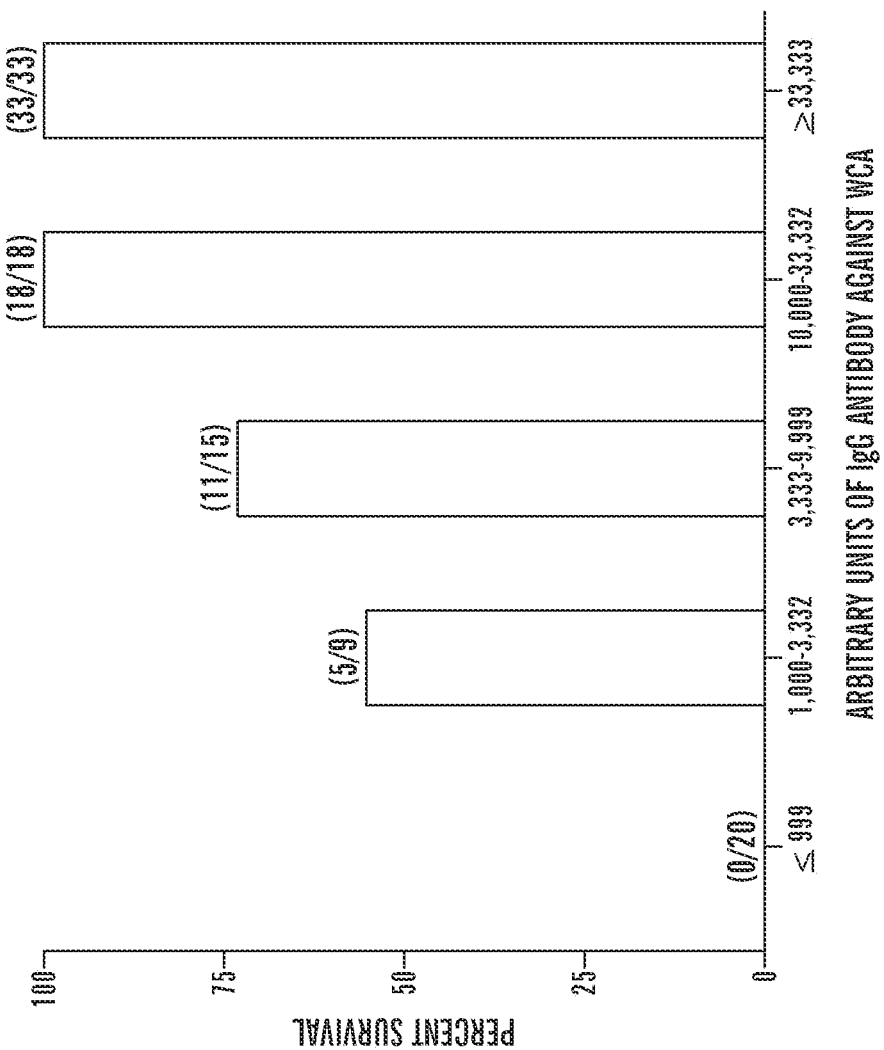

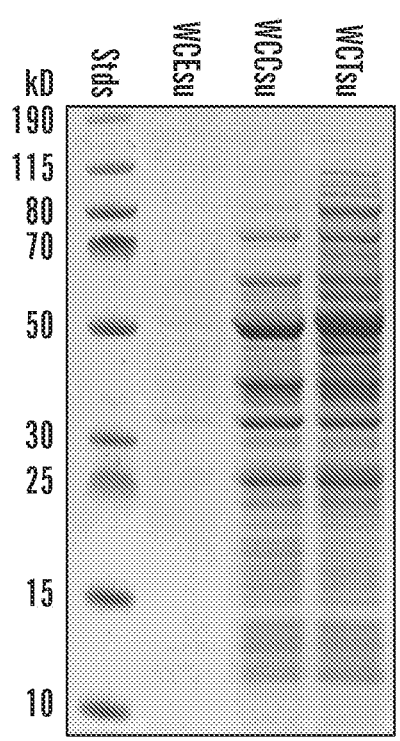 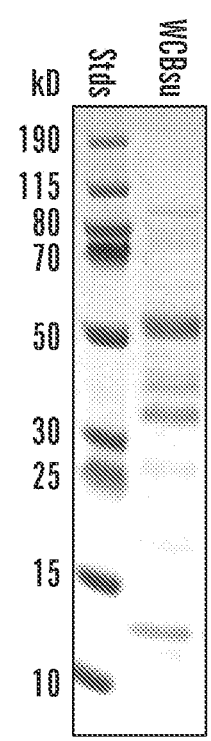
*FIG. 3A*  *FIG. 3B*

SELECTIVELY DISRUPTED WHOLE-CELL VACCINE

CROSS REFERENCE TO RELATED APPLICATIONS

This application is a 35 U.S.C. §371 National Phase Entry Application of International Application No. PCT/US2010/052298 filed Oct. 12, 2010, which designates the U.S., and which claims benefit under 35 U.S.C. §119(e) of U.S. Provisional Patent Application No. 61/250,348, filed 9 Oct. 2009, and U.S. Provisional Patent Application No. 61/380,429, filed 7 Sep. 2010, the contents of which are incorporated herein by reference in their entireties.

GOVERNMENT SUPPORT

This invention was made with U.S. government support under R01 AI066013, AI067737-01 and AI51526-01, awarded by The National Institutes of Health. The U.S. government has certain rights in the invention.

FIELD OF THE INVENTION

The present invention relates to molecular genetics, immunology, and bacteriology. More specifically, an embodiment of the present invention provides for a whole-cell immunogenic preparation that confers synergistic antibody-mediated and T lymphocyte-mediated immune responses. In the case of pneumococci, the whole-cell immunogenic preparation elicits synergistic, antibody- and T lymphocyte-mediated (including IL-17A-mediated) protection against lethal infection and mucosal pneumococcal colonization.

BACKGROUND

Infection with *Streptococcus pneumoniae* (pneumococcus) is a major cause of morbidity and mortality worldwide, and causes serious disease in children and the elderly, including pneumonia, meningitis and bacteraemia, and some less severe infections such as otitis media. Almost one million children in the developing world die of infections due to pneumococcal disease each year.

The rapid emergence of multiple-drug-resistant strains of *S. pneumoniae* has limited the effectiveness of antibiotics and stimulated renewed interest in the prevention of pneumococcal infections with vaccines. Licensed pneumococcal vaccines consist of injectable polyvalent mixtures of serotype-specific capsular polysaccharides or capsular polysaccharide-protein conjugates and are therefore effective only against serotypes included. For example, although the 7-valent pneumococcal conjugate vaccine (PCV7) has significantly reduced the incidence of invasive pneumococcal disease due to vaccine-type (VT) strains, recent studies have shown that non-VT serotypes are gradually replacing VT serotypes, potentially limiting the usefulness of the vaccine. This has led to the evaluation of whether pneumococcal colonization can be prevented by immunization with serotype-independent antigens. For example, mucosal immunization with some proteins conserved widely throughout the *S. pneumoniae* species has been shown to elicit systemic and mucosal antibodies and to confer protection against pneumococcal disease and colonization.

Work continues to identify immunogenic compositions, including pneumococcal polysaccharides and proteins, that raise both antibodies and robust T lymphocyte-mediated immune responses to all serotypes. An alternative approach uses killed pneumococcal cells—which present multiple serotype-independent antigens—as an inexpensive vaccine, but the immunogenicity of these compositions has not been adequately explored previously. Hence, there remains a need for new approaches to the preparation of whole-cell pneumococcal vaccines, and an understanding of the mechanisms of immunity associated therewith.

SUMMARY

The embodiments presented herein provide for immunogenic compositions comprising Gram-positive bacterial (e.g., pneumococcal) cell preparations that have been killed by methods that increase exposure of immunogenic components that are not found in preparations killed by conventional methods, and that retain the advantage of bacteria-sized particles for antigen uptake. The immunogenic compositions comprise both the cellular and supernatant (e.g., solvent or aqueous phase) fractions of the killed, whole-cell preparation, and exhibit synergistic immunogenic properties compared with the cellular and soluble fractions administered individually. These immunogenic compositions do not depend upon the pneumococcal capsular polysaccharide and provide immunogenicity independently of capsular serotype.

In some embodiments, the pneumococcus is a non-capsulated variant. In some embodiments, the pneumococcus is a variant lacking the lytA gene, which specifies the main autolysin, thus cultures of this variant pneumococcus can grow to relatively high density without auto-lysing. In other embodiments, the gene for pneumolysin (PdT, a cytotoxin) has been replaced to specify a mutated protein PdT, which is non-toxic but still a TLR4 agonist (with capacity to engage the innate immune system).

In one embodiment of the present invention, the pneumococcal cells are treated (killed) with an agent, such as beta-propiolactone (BPL), that (a) partially disrupts the cells in a way that releases a variety of protective immunogens that are recognized as soluble molecules; (b) can be removed without washing the harvested cells so that immunogens released into the suspending fluid can be retained easily in the preparation; and (c) maintains the overall structure of the pneumococcal cell to facilitate uptake by those components of the afferent limb of the immune system responsive to bacteria-sized particles bearing TLR ligands. In similar embodiments, the agent is chloroform or trichloroethylene.

In another embodiment, the preparation of the whole-cell immunogenic composition is prepared by a method comprising sonication.

The immunogenic compositions of the present invention can be administered by injection, and also by nasal, sublingual, buccal, or transdermal routes. The immunogenic compositions may be combined with appropriate adjuvants, such as alum or enterotoxin-related molecules, e.g., cholera toxin.

The pneumococcal immunogenic compositions described herein are relatively simple and inexpensive to manufacture, and are more potent than previously described pneumococcal vaccines. For example, doses of a little as 1.7 micrograms significantly protects mice against fatal experimental pneumonia.

DESCRIPTION OF THE DRAWINGS

FIGS. 2A-2B show the relation of the pre-challenge immunological responses to protection in the colonization and aspiration-sepsis models. WCB (WCV prepared using beta-propiolactone) at doses of 1, 10, or 100 μg was adsorbed to $Al(OH)_3$ (0.21 mg Al/dose) and injected subcutaneously thrice at 2-week intervals. FIG. 2A shows the relation of colonization with serotype 6B and IL-17A responses; colonization was inversely related to the prechallenge concentration of IL17A. FIG. 2B shows the relation of survival in the aspiration-sepsis model to the pre-challenge titer range of IgG anti-WCA (whole cell antigen). Eight days post-3rd dose, the mice were anaesthetized with isofluorane and given $10^6$ CFU of serotype 3 strain WU2 in 100 μl PBS, intranasally (i.n.). This model typically induces sepsis in the majority (>90%) of naïve mice within 1 week after challenge. Survival increased with the titer and was 100% at titers>10,000 arbitrary units.

FIGS. 3A and 3B show radiographs of SDS-PAGE of proteins released from pneumococcal cells (specifically, RM200 cells). FIG. 3A shows centrifugal supernatants (su) (16,000×g; for 5 min) of cell suspensions after killing with chloroform (WCCsu) or with another organic solvent, trichloroethylene (WCTsu); neither preparation was washed post-killing. Comparison is made with the supernatant of a suspension of ethanol-killed vaccine (WCEsu), which had been washed in the course of conventional vaccine preparation; only a faint trace of supernatant proteins remain. FIG. 3B shows the supernatant of cells killed by beta-propiolactone (WCBsu), which were similarly not washed post-killing.

FIG. 5A shows priming for IL-17A responses to WCA in vitro by blood samples taken 2 weeks post-2nd injection; FIG. 5B is IgG antibody to WCA assayed by ELISA in those blood samples. FIG. 5C shows clearance of serotype 6B from the nasopharynx. In this and subsequent Figures, unless indicated, the significance of differences was compared to adjuvant alone, calculated by Mann-Whitney U, is shown by asterisks: * p<0.05,  p<0.01 and * p<0.001. By all three criteria, the immunogenicity was greatly increased by the $Al(OH)_3$.

FIGS. 6A-6B present a comparison of WCC with antigen made with beta-propiolactone-killed cells (WCB); and role of the CD4+ cells in the colonization model. Schedule, assays, and challenge were as in FIG. 5. FIG. 6A shows priming for IL-17A; the dose-responses show equal immunogenicity of WCB and WCC. FIG. 6B shows clearance of a serotype 6B strain from the nasopharynx; by this criterion WCB and WCC were likewise equally potent. Dependence upon CD4+ cells was evaluated in a group of WCC-immunized animals given CD4 antiserum 1 day prior to and two, five, eight days after challenge (in the column indicated by a-CD4); in these animals the enhanced clearance was abrogated.

FIG. 7A shows that in the 3-injection schedule, 8 days post-3rd dose, the mice were anaesthetized with isofluorane and given $10^6$ CFU of strain WU2 in 100 μl PBS i.n. Survival curves are shown. Mice alive after seven days were sacrificed and cultured for pneumococcal bacteremia: the only bacteremic animals were two of the three $Al(OH)_3$-only controls. The 10-ug dose, like the 100-ug dose was completely protective. Dependence of the protection upon CD4+ cells was evaluated in the indicated group that was given CD4 antiserum 1 day prior to and 3 days after challenge; in contrast to the colonization model, there was no detectable abrogation of protection, indicating that the antibody response alone was adequate for protection FIGS. 7B and 7C show a simpler, 2-injection schedule. FIG. 7C shows that in plasma samples taken 2 days pre-challenge, all animals with the 100-ug dosage had titers exceeding 10,000, while not all did so with the 10-ug dosage. The mice were challenged 9 days post-2nd dose, and survival is graphed as in 7A; protection was partial with the 10-ug dosage and complete with the 100-ug dosage, congruent with the antibody responses.

FIG. 8A shows a dose-dependent increase in serum IgG antibody titers against WCA at day 43. FIG. 8B reflects passive protections: Pools of the day-45 sera from $Al(OH)_3$ and $Al(OH)_3$-adsorbed WCB at dose 500 μg-immunized rabbits were tested for passive protection in the mouse pneumonia model with serotype 3. Serum was heated at 56°

C. for 30 min to inactivate complement. Mice were given 200 μl of either pool with 300 μl PBS intraperitoneally one day before being challenged with strain WU2 as described in FIG. 7A. Survival curves show complete protection by the immune serum. FIG. 8C shows an opsonophagocytic killing assay. Heat-treated sera from rabbits immunized three times with alum alone or alum-adsorbed WCB (500 μg per dose) were used in a surface killing assay using a serotype 6B pneumococcal strain (0603). At the three dilutions tested (⅕, 1/20 and 1/80), immune sera significantly increased opsonophagocytic killing of pneumococci compared to pre-immune sera at the same dilution. **P<0.008 by Mann-Whitney U.

FIG. 9A: IgG antibody response; FIG. 9B: IL-17A response. By both criteria the optimal dosage based upon pre-killing viable cell count was 3.3 E7, which corresponds to a protein dosage of 33 micrograms. A statistically significant IL17A response was produced by 3.3 micrograms but not by 1 microgram, while a significant antibody response was produced by as little as 1 microgram. As used herein, and throughout the specification, unless otherwise specified, $E5=10^5$, $E6=10^6$, $E7=10^7$, $E8=10^8$, $E9=10^9$, $E10=10^{10}$, etc.

FIG. 10A plots the titers of plasma antibody to whole-cell antigen (WCA) (here the buccal route is described as "oral"); there was a measurable antibody response to WCC by both routes, although much less than by the subcutaneous route—as shown at the left; FIG. 10B reflects priming for IL-17A responses to WCA by blood cells in vitro (pg/ml, y-axis); there was a dose-dependent response by both routes.

FIG. 12C shows priming for IL-17A responses to WC antigen by blood cells in vitro data comparing TCI with i.n. administration. FIG. 12D: Clearance of serotype 6B colonization data comparing TCI with i.n. administration. For other details, see description of FIGS. 1A-1E. * P<0.05;  P<005; * P<0.0005.

DETAILED DESCRIPTION

Figure 1A:
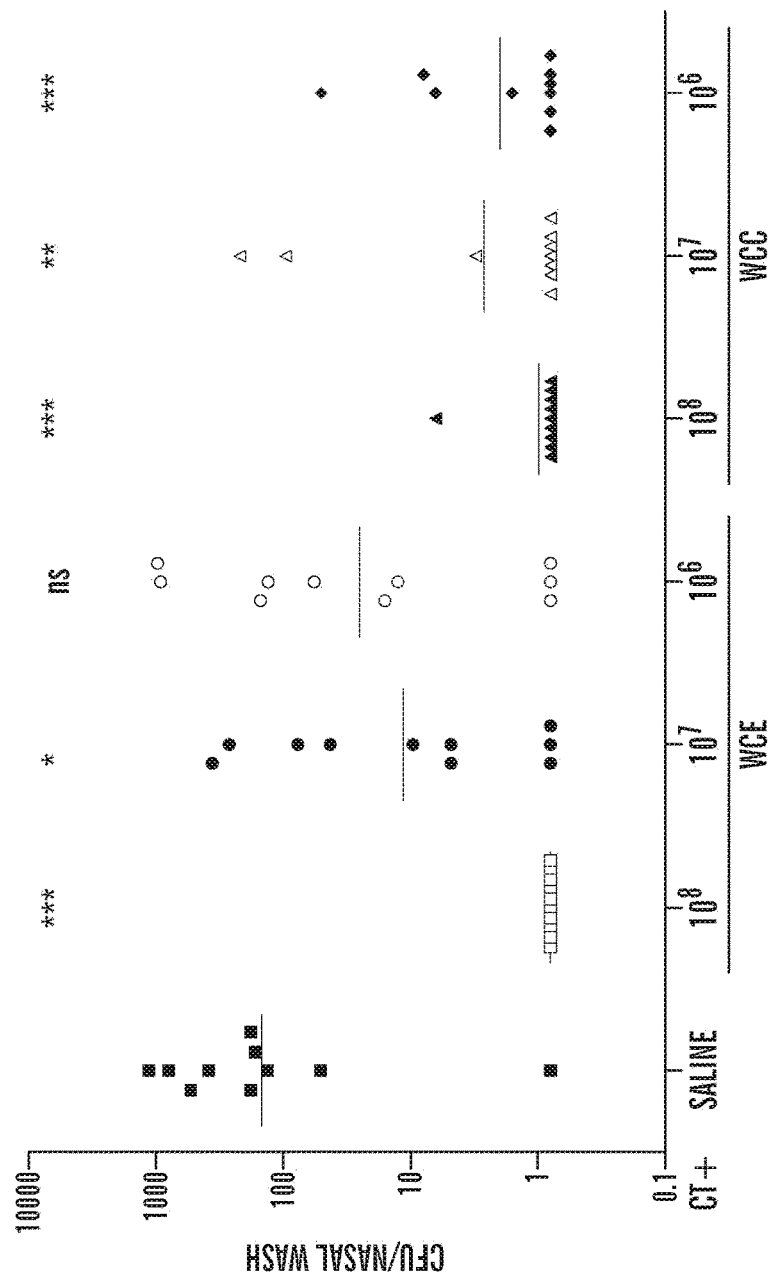
FIG. 1A shows the enhanced protection by a pneumococcal whole-cell (WC) vaccine prepared using chloroform (WCC) compared to ethanol-treated cells (WCE), at doses indicated (x-axis). Vaccines were given to mice twice, intranasally, at weekly intervals at the dosages indicated, using 1 μg of cholera toxin (CT) as adjuvant. Mice were intranasally challenged with a different serotype (serotype 6B) 3 weeks after the last immunization. Determination of colony-forming units (CFU) per nasal wash was 1 week post-challenge. WCC was significantly protective at doses 10 to 100-fold lower than WCE.

The invention presented herein is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

The present invention pertains to the selective disruption of whole-cell pneumococcal preparations. Although numerous microbial inactivating agents are known within the art, the present invention provides for select disruption and inactivation, i.e., in such a manner that allows for the preparation of immunogens that are highly effective in elicitation of both T-lymphocyte-mediated and antibody-mediated immune responses. Utilizing the techniques and agents in the manner described herein, whereby the bacterial preparation is selectively inactivated and disrupted, and exhibits unexpected immunogenicity, is not known in the art.

*S. pneumoniae* (pneumococcus) imparts a major disease burden among children in low-income countries. O'Brien et al., 374 Lancet 893 (2009). Capsular polysaccharide conjugate vaccine provides type-specific protection but has the disadvantages of limited serotype coverage, serotype replacement, and high cost of production, storage, and injection. Hanage, Future Microbio. 23 (2008); Ray, 1 Vaccines 65 (2002). Therefore, potentially more economical serotype-independent vaccines based upon species-common protein antigens are being pursued. Tai, 32 Crit. Rev. Microbio. 139 (2006). In one such approach, killed cells of noncapsulated pneumococci were studied with the intent of maximizing the exposure of species-common subcapsular antigens. It had been well known that inactivated bacterial cells can be used as vaccines; killing by heat, phenol, formalin, or UV radiation have been used for such inactivation. With noncapsulated cells of pneumococci, however, killing the cells with 70% (vol/vol) ethanol at 4° C. produces a more immunogenic antigen than traditional methods of inactivation such as heat, etc. This antigen preparation, was called "whole-cell antigen" (WCA) and called "whole-cell vaccine" (WCV) when formulated with a suitable adjuvant. For clarity here this antigen is designated WCE to denote the inactivation with ethanol. Intranasal (i.n.) application had been examined initially, since this route is effective for inducing both systemic and mucosal immunity. Vaccination i.n. with WCE plus cholera toxin (CT) as a mucosal adjuvant prevents fatal serotype 3 pneumonia in rats and reduces nasopharyngeal (NP) produced by non-lethal intranasal challenge of mice with type 6B pneumococcus. Malley et al., 69 Infect. Immun. 4870 (2001). The latter challenge was relevant because it was known that nasopharyngeal colonization is the necessary first step in pneumococcal infection. Austrian, 18(A) J. Antimicrob. Chemother. 35 (1986). This challenge, whether by strains of serotypes 6B or 23F, produces colonization of the middle ear as well as NP, and both are reduced by WCE. Malley et al., 72 Infect. Immun. 4290 (2004). Although the levels of serum antibodies are raised by the i.n. vaccination, protection against colonization is induced in mice in the absence of antibodies by a CD4 T-cell-dependent, interleukin 17A (IL-17A)-mediated mechanism. Lu et al., 4 PLoS Pathog. e1000159 (2008); Malley et al., 102 PNAS 4848 (2005). As few as $10^7$ cells (ca. 10 μg of protein) of WCE, given thrice sequentially, are protective in the colonization model. Trzcinski et al., 76 Infect. Immun. 2678 (2008). These previous studies made WCE with strain Rx1AL, expressing native pneumolysin, a potent cytolysin. As an alternative approach, described herein and anticipating human studies, a derivative of pneumolysin (PdT), with mutations W433F, D385N, and C428G (which render the molecule nonhemolytic and unable to activate complement (Berry et al., 63 Infect. Immun. 1969 (1995)), but maintain its TLR4 agonistic properties (Malley et al., 100 PNAS 1966 (2003)), can be used. Previously, cells were grown in Todd-Hewitt-yeast broth, which contains beef heart infusion. Additionally, to avoid any hazard of bovine components cells grown in a soy-based medium (Liberman et al., 35 J. Ind. Microbio. Biotech. 1441 (2009)) can be used.

One drawback of WCE is that the 70% ethanol must be separated from the killed cells, for example by centrifugation. The present invention also provides techniques to avoid the challenge of safe handling and disposal of large volumes of ethanol, providing for at least three alternative agents of inactivation that are bactericidal at low concentration: chloroform, trichloroethylene, and beta-propiolactone. Because chloroform and trichloroethylene are both highly volatile and beta-propiolactone is inactivated by warming, these agents may be removed without post-inactivation separation of the cells from the aqueous phase, which also permits, for the first time, convenient examination of soluble components released from the killed cells. Soluble components produced by sonication also are examined as presented herein.

The possible side effects of enterotoxins as adjuvants (Mutsch et al., 350 N. Engl. J. Med. 896 (2004)), and other problems with intranasal vaccination prompted the consideration of genetically detoxified enterotoxin derivatives and of the buccal and sublingual routes of administration. Transdermal immunization was also examined with sonicated antigen preparations. These varied immunization procedures were surveyed for protection against colonization, evident as acceleration of nasopharyngeal clearance after intranasal challenge with a strain of serotype 6B (Lu et al., 2008). The results presented herein indicate that the cells can be inactivated by several agents to generate a potent whole-cell antigen that could be given in a variety of ways to accommodate preferences of a particular vaccination program.

For example, beta-propiolactone (BPL) was used for the disruption of an unencapsulated whole cell *S. pneumoniae* strain. BPL treatment results in two components with immunogenic activity. The partially disrupted cell remains structurally intact post-BPL treatment as a cellular fraction. This cellular fraction is somewhat effective in antibody induction and potently effective in IL-17A induction, which thus facilitates phagocytic killing of pathogenic bacteria (e.g., by polymorphonuclear leukocytes) and subsequent antigen presentation. Additionally, BPL disruption of *S. pneumoniae* releases antigens into the soluble (aqueous) fraction that are protective in a serotype-independent manner. These soluble components can be retained in the immunogenic composition by hydrolyzing the BPL and negating the procedural need for their removal from the cells. The effectiveness of this soluble fraction has also been experimentally demonstrated herein. Thus, a unique and serotype independent two-pronged T lymphocyte-mediated and antibody-mediated immunity is engaged upon inoculation of the treated bacterial preparation.

Previously, mucosal immunization with a killed whole-cell pneumococcal vaccine, given with enterotoxin-related adjuvants, has been shown to confer multi-serotype protection against colonization of the nasopharynx and middle ear in mice. In addition to novel mucosal immunization strategies, that may be difficult to implement, the present embodiments provide for subcutaneous or intramuscular injection. For example, pneumococcal strain RM200 was engineered to be capsule-negative, autolysin-negative, and to express a non-toxic mutant pneumolysoid. Cultures were grown in bovine-free soy-based medium, killed with chloroform or beta-propiolactone, and injected into C57131/6 mice without or with aluminum adjuvant Protection against colonization was mechanistically dependent on the presence of CD4+ T-cells at the time of challenge; in contrast, in the type 3 aspiration-sepsis model, CD4+ T-cells were not required for protection at the time of challenge, suggesting that antibody alone was sufficient to protect against death in this model. Rabbits receiving sequential intramuscular injections in a pilot toxicity study displayed local reactogenicity at injection sites but no clinical signs. The rabbit antiserum thus produced was active in an in vitro phagocytic killing assay and passively protected mice in the type 3 aspiration-sepsis model.

The present invention addresses major needs within the field of pneumococcal vaccines: Current vaccine compositions utilize serotype-specific capsular polysaccharides to confer immunity to specific serotypes, whereas the proposed invention is not based on capsular polysaccharide-induced responses. Thus, the resulting disrupted cell and soluble antigens can be used in conjunction to confer the advantage of multi-serotype vaccine applicability. This is especially useful where other vaccines are susceptible to gaps in coverage due to serotype selection. Second, the current cost of PREVNAR®, a commonly used vaccine, is $65 per dose, whereas one estimate proposes that the cost of producing the vaccine described herein is $0.20 per dose. Thus, the present embodiments meet potent biological and economic based needs within the field.

Specifically, it was known that, when administered intranasally, WCE protects mice against NP colonization by priming for elaboration of the phagocytosis-promoting cytokine IL17A (as demonstrated by an in vitro assay with blood samples) and that the accompanying antibody response is unnecessary. Lu et al., 4 PLoS Pathog. e1000159 (2008); Malley et al., 102 PNAS 4848 (2005). In the present invention the pneumococcal vaccine strain RM200 was killed by chloroform (C), trichloroethylene (T), or beta-propiolactone (B) to make preparations WCC, WCT, and WCB, respectively. For vaccination experiments the killed cell suspensions were lyophilized in single-use aliquots with sucrose as a stabilizer, and were rehydrated just prior to the test.

These preparations were compared with WCE, each given i.n. twice with CT adjuvant, in acceleration of clearance of an intranasal challenge with a pneumococcal strain of serotype 6B and in priming for IL-17A responses in vitro. By both criteria, WCC, WCT, and WCB were more potent than WCE. Specifically, FIG. 1A shows that WCE was protective (i.e., significantly reduced number of CFU recovered from the nasopharynx of mice challenged intranasally with 6B strain 0603) at doses of $10^8$ and $10^7$ per immunization but not at $10^6$, while WCC was protective at $10^6$ as well (dosage expressed as number of CFU before killing; this corresponds to about 1.7 micrograms dry weight or 1 microgram of protein). WCC, like WCE, primed for IL-17A expression by T-cells in vitro: 1 week prior to challenge, the IL-17A expression of individual WCC-immunized mice was negatively correlated with the CFU recovered postchallenge (FIG. 2A; Spearman p=−0.54, P=0.0007).

Figure 1B:
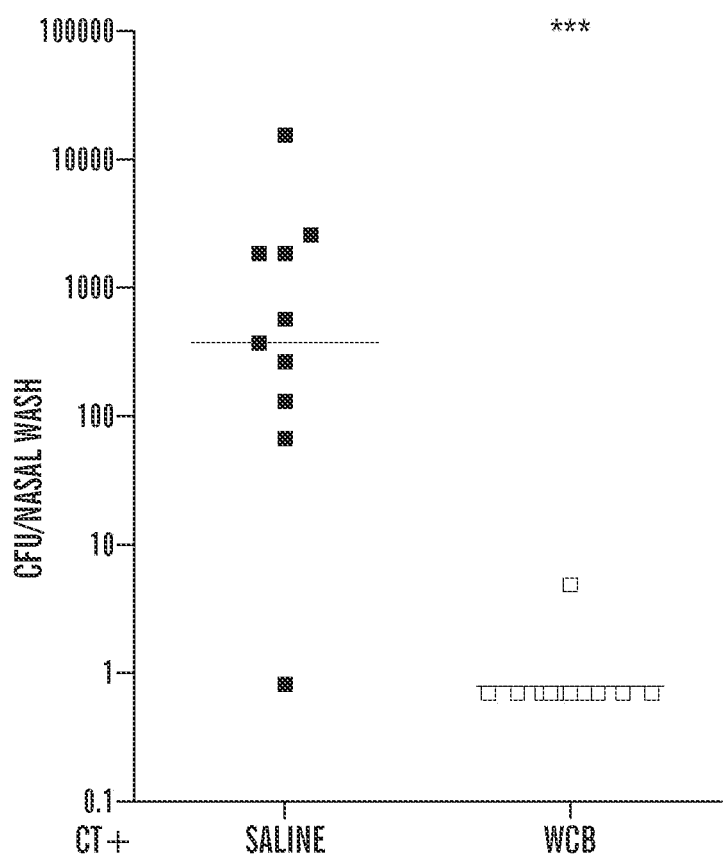
FIG. 1B shows protection by WCB (WC vaccine prepared using beta-propiolactone) at $10^8$ dosage.
Figure 1C:
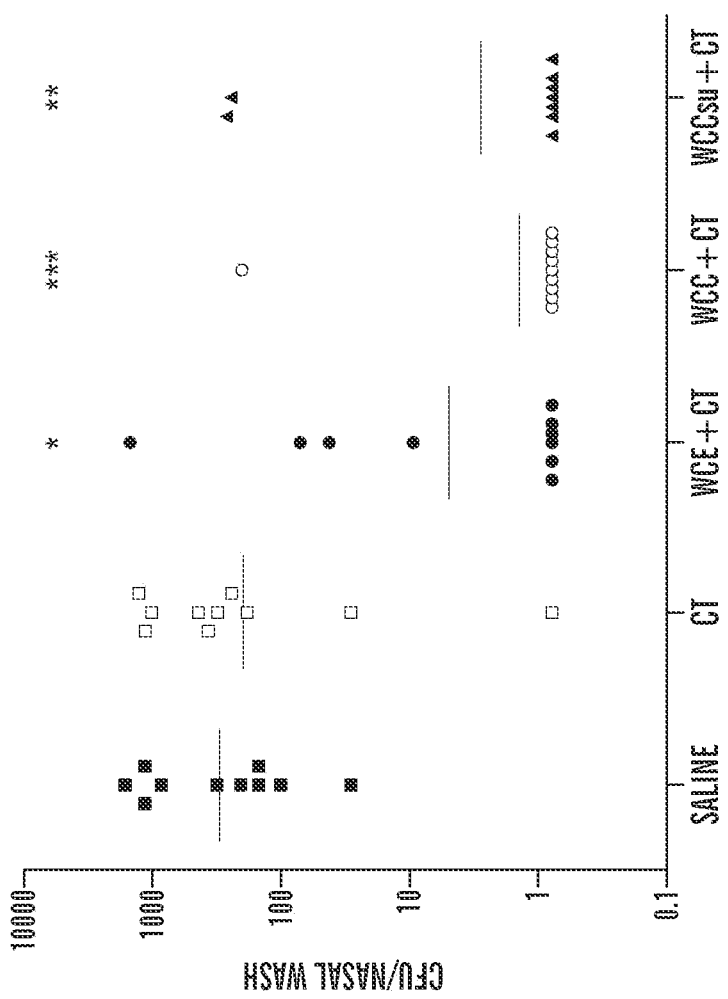
FIG. 1C presents a comparison of WCE, WCC, and the centrifugal supernatant fraction of WCC (WCCsu); the doses were $10^8$ of WCE or WCC or the equivalent amount of supernatant of WCC. The indicated groups received CT (cholera toxin) as adjuvant; one control group received saline with no CT; WCCsu was protective with a statistical significance greater than WCE.
Figure 6A:
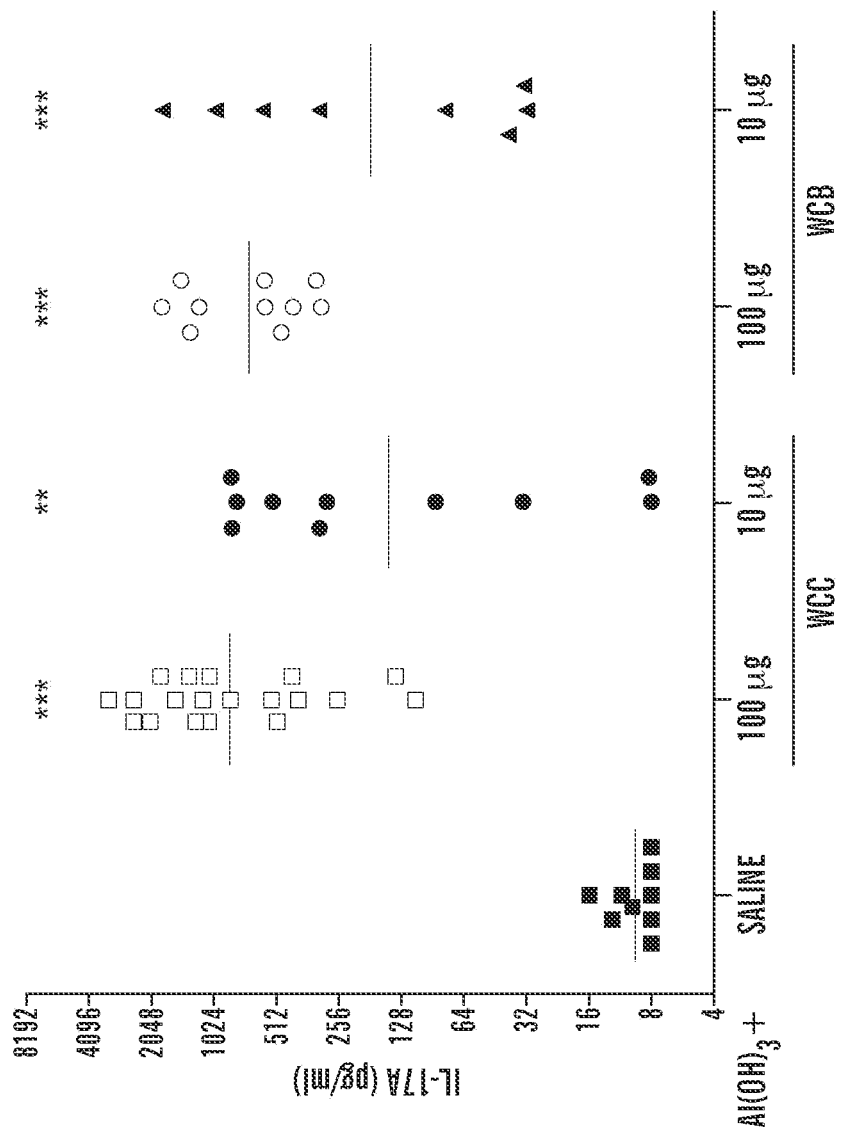
(FIGS. 6A, 6B show its potency equal to WCC in a separate test).
Figure 6B:
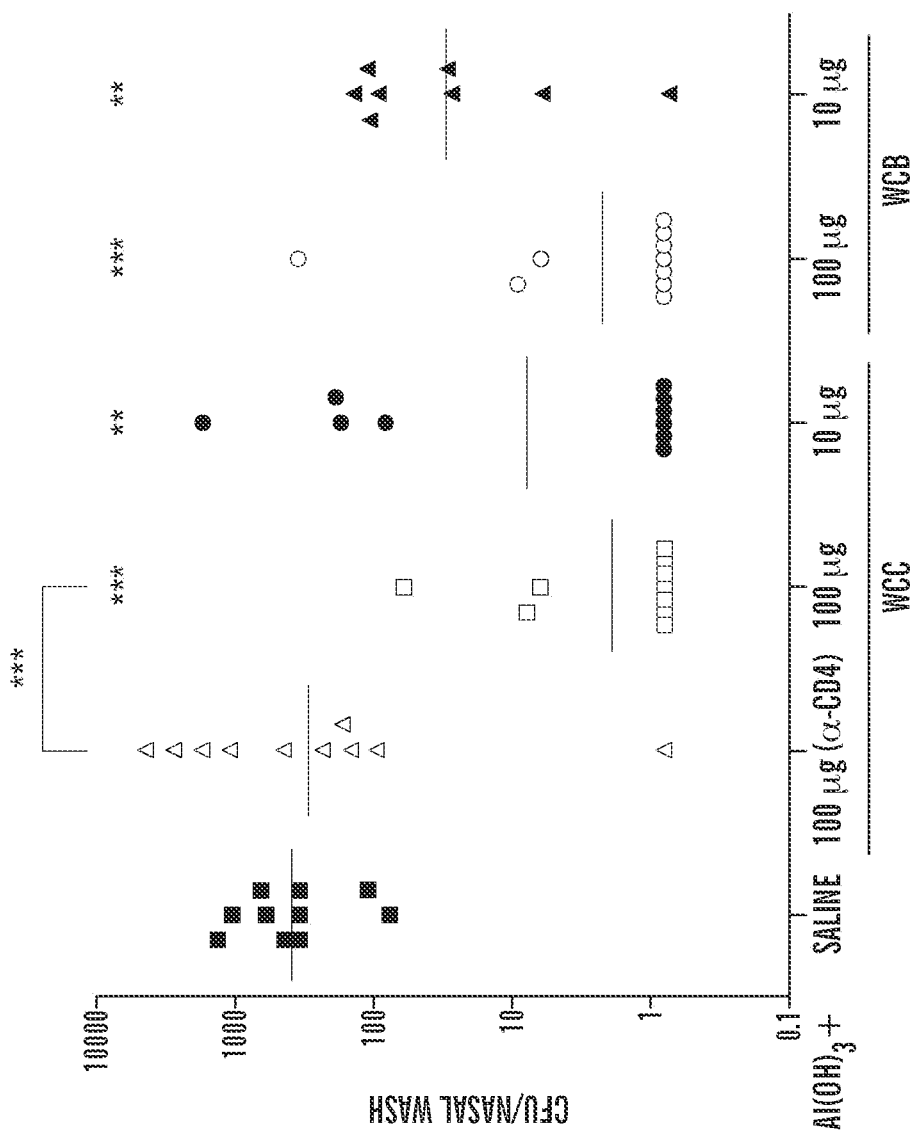

In a separate experiment, WCT was significantly protective at dosage 10-100 fold lower than WCE. Thus, WCC and WCT appeared about 10-fold more potent than WCE. WCB was likewise protective when administered intranasally: it was protective against colonization (FIG. 1B) and active in IL-17A priming; the protection was correlated with the IL17A assay. In a separate experiment, WCB was shown to have quantitative potency similar to WCC (FIGS. 6A, 6B).

Killing of pneumococcal RM200 cells in aqueous suspension with any of these agents releases a variety of proteins into the soluble (aqueous) phase. Because ethanol is miscible with and difficult to remove from water, ethanol-killed cells must be separated from the aqueous phase so as not to contaminate the WCE vaccine with a noxious solvent. In contrast, the immiscible solvents chloroform and trichloroethylene can easily be removed from the aqueous phase, and beta-propiolactone can be easily decomposed into harmless components; so after killing by these agents, the water-soluble phase can be retained with the cells in the vaccine. When the vaccines are analyzed by electrophoresis after centrifugal removal of the cells from the vaccine suspensions, the supernatant fractions of WCC, WCT, and WCB display obviously the variety of released proteins, while WCE (obtained from the previously phase-separated WCE vaccine) as expected displays only a faint trace of such proteins. The released proteins have been shown to have substantial protective activity per se and thus evidently contribute to the greater potency of the presently disclosed vaccine preparations relative to WCE.

Specifically, the pneumococcal vaccine strain RM200 was grown to late log phase in a soy-based medium followed by washing and concentration to an $A_{600}$ of 32 in lactated Ringer's solution. Killing was done by stirring at 4° C. with chloroform (C) (1/40 [vol/vol]) for 2 hours trichloroethylene (T) (1/40 [vol/vol]) for 2 hours or beta-propiolactone (B) (1/4,000 [vol/vol]) for 24 hours The cells were not further washed: C and T were removed by lyophilization, and B was decomposed by 2 hours of incubation at 37° C. before lyophilization. The resulting vaccine antigen preparations are referred to as WCC, WCT, and WCB, respectively. To examine for release of material from the cells, samples of lyophilized WCE, WCC, WCT, and WCB were suspended in LR at an A600 of 32, vortexed at 25° C. for 1 minute, and then centrifuged at 16,000×g for 5 min. The total protein content of the supernatants was approximately 15% of the total protein of the non-centrifuged suspensions. SDS-PAGE (FIG. 3A) showed a large number of soluble proteins in the supernatants (designated by the subscript "su") of WCC and WCT, while WCE (which had been previously centrifuged after killing to remove the large volume of 70% ethanol present) contained only a trace of such proteins. When a suspension of cells in 70% ethanol was examined without centrifugation, however, a comparable mixture of proteins, which ordinarily would be lost in the preparation of WCE, was shown to have been solubilized (not illustrated). FIG. 3B shows that a number of soluble proteins were likewise present in WCB. We have shown that the centrifugally separated aqueous phase of chloroform-killed cells ("WCCsu"), like the unseparated vaccine WCC, is highly protective against colonization. Similar results are demonstrable with WCB and WCBsu (not illustrated). Thus, after killing RM200 cells with agents permitting retention of released components, the soluble phases contribute to protection when administered by the intranasal route.

There are many potential advantages in considering a pneumococcal vaccine such as WCV for mucosal administration. Holmgren & Czerkinsky, 1 Nat. Med. S45 (2005). The World Health Organization's "Target Product Profile" for Advance Market Commitment for Pneumococcal Vaccine (WHO, *Target Product Profile (TPP) for the Advance Market Commitment (AMC) for Pneumococcal Conjugate Vaccines* (2008)), prefers subcutaneous or intramuscular injection; thus it was cogent to test the presently disclosed preparations as injectable vaccines, using currently approved aluminum adjuvants. Subcutaneous injections protected mice against intranasal colonization, which necessarily precedes pneumococcal diseases. Austrian, 18(A) J. Antimicrob. Chemother. 35 (1986). Adsorption on Al(OH)$_3$ greatly increased the potency.

In addition to the present serotype 6B colonization model, which is non-lethal, a lethal serotype 3 model was used: intranasal challenge of anaesthetized mice with a highly encapsulated serotype 3 strain produces bacteremia and death. Here, WCC or WCB by the s.c. route are likewise potent: three sequential injections of as little as 1 μg protein, or two injections of 10 μg, were significantly protective. In this model, the serum antibody response, which is unnecessary for clearance of pneumococci from the nasopharynx (Malley et al., 102 PNAS 48 (2005)), appears to participate in protection, as shown both with non-abrogation of the protection by CD4 antibodies and "passive protection" by transfer to the mice of serum from vaccinated rabbits.

Figure 5A:
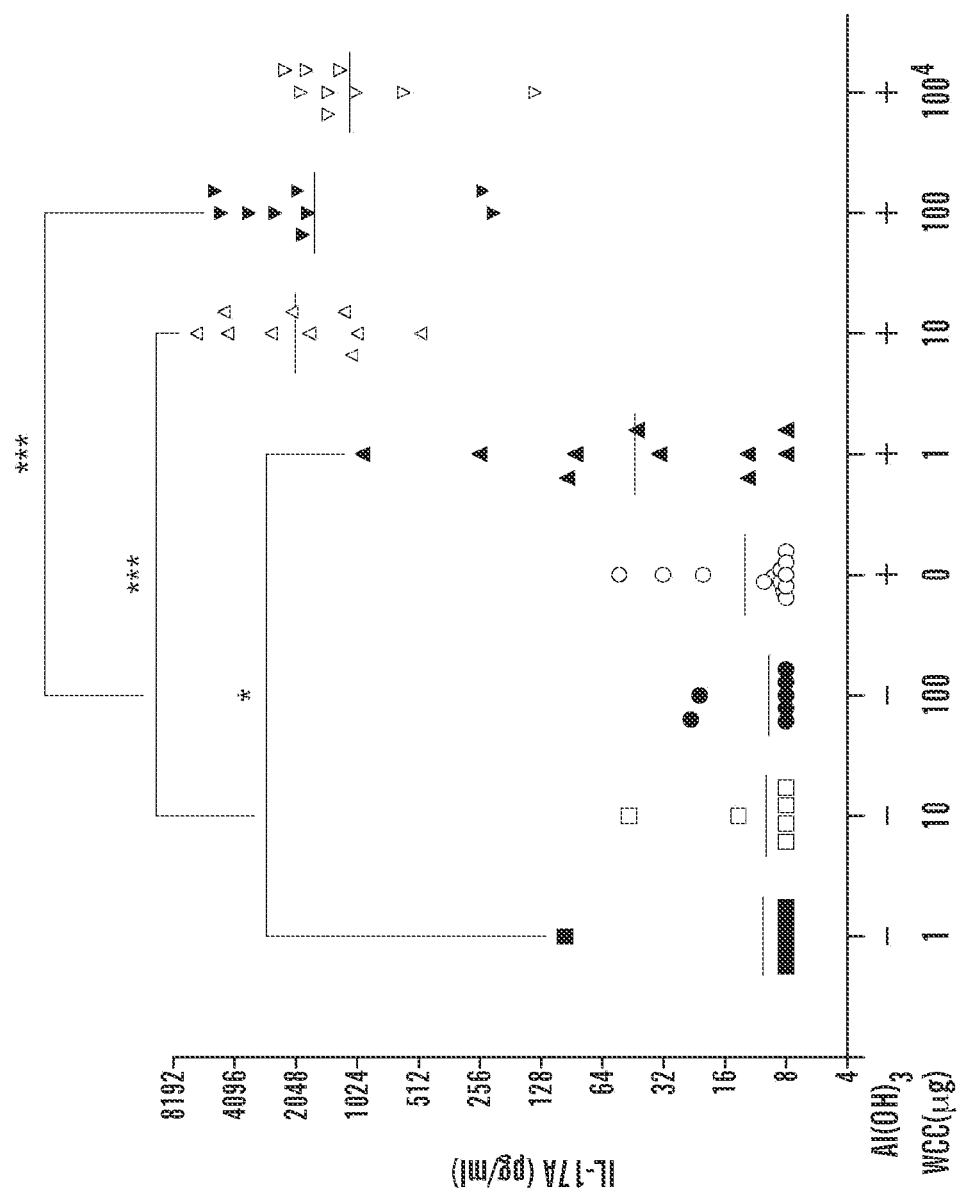
FIGS. 5A-5C show the effect of $Al(OH)_3$ adsorption on the immunogenicity of WCC. The antigen was incubated 18 hours at 4° C. with gentle mixing so as to provide 1, 10, or 100 μg of protein and 0.21 mg of Al per 0.2 ml dose. Adsorbed or nonabsorbed antigen or $Al(OH)_3$ alone was injected in mice, under the skin in the lower back area, three times at 2-week intervals. The mice were challenged 2 weeks post-3rd injection with pneumococcal type 6B strain 0603. Ten days post-challenge the CFU recovered from nasal wash samples was determined. In data column 8, the WCC-$Al(OH)_3$ preparation was incubated 1 month at 37° C. then stored at 4° C. before injection (Δ superscript).

Specifically, for evaluation by immunological assays and protection in the colonization model, ascending doses of WCC (1 μg, 10 μg, and 100 μg) were tested in a three-injection sequence without and with adsorption onto Al(OH)$_3$ (0.21 mg Al per dose). Without adjuvant there was no measurable IL-17A response (FIG. 5A), while with Al(OH)$_3$ there was a significant response even to the 1 μg dose.

Figure 5B:
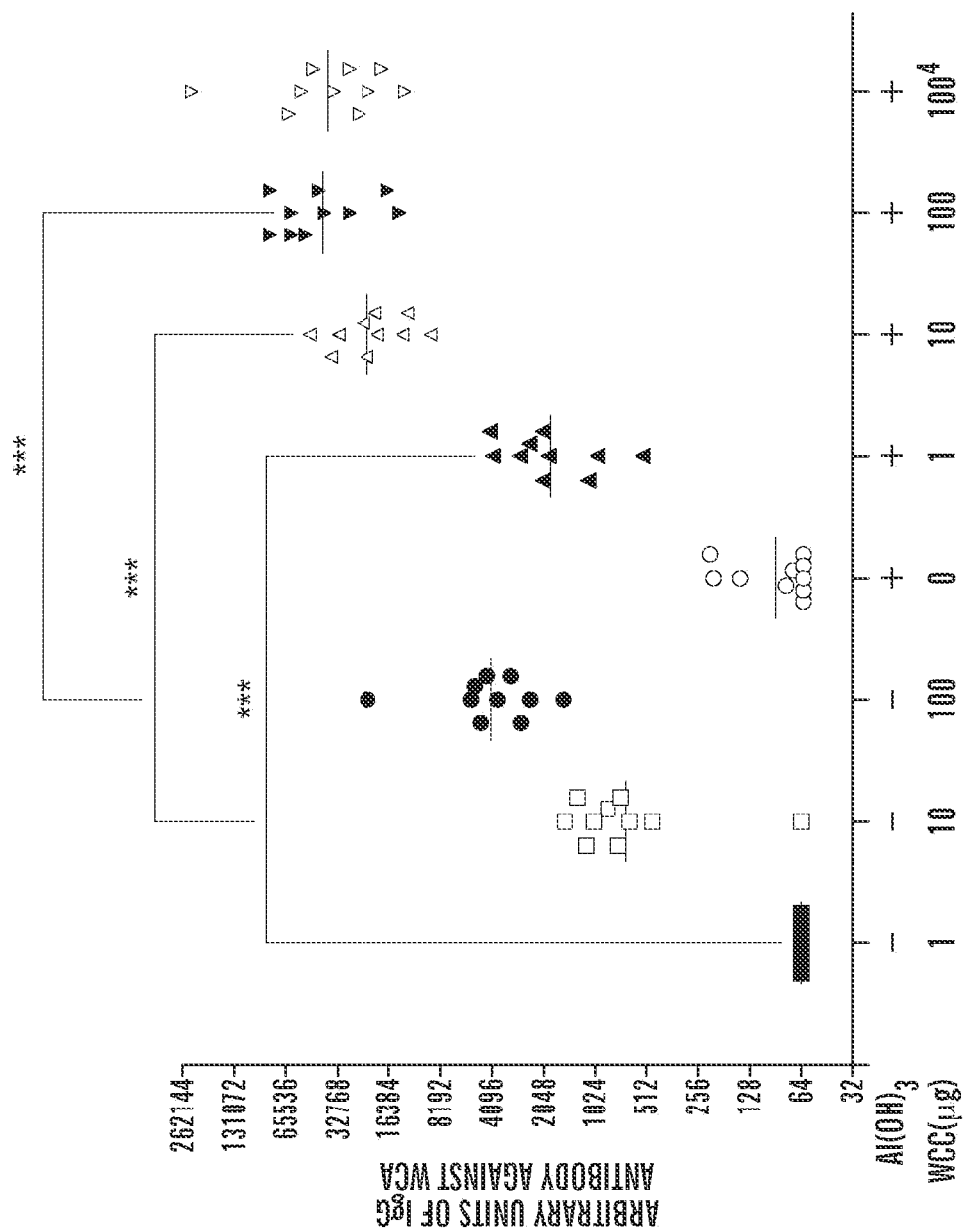

The plasma IgG antibody was determined by ELISA with WCC as the coating antigen and HRP-conjugated secondary antimouse IgG. Without and with adsorption there were dose-dependent antibody responses, but with about 100-fold potentiation by the Al(OH)3 (FIG. 5B). The antibody response included both IgG1 and IgG2c.

Figure 2A:
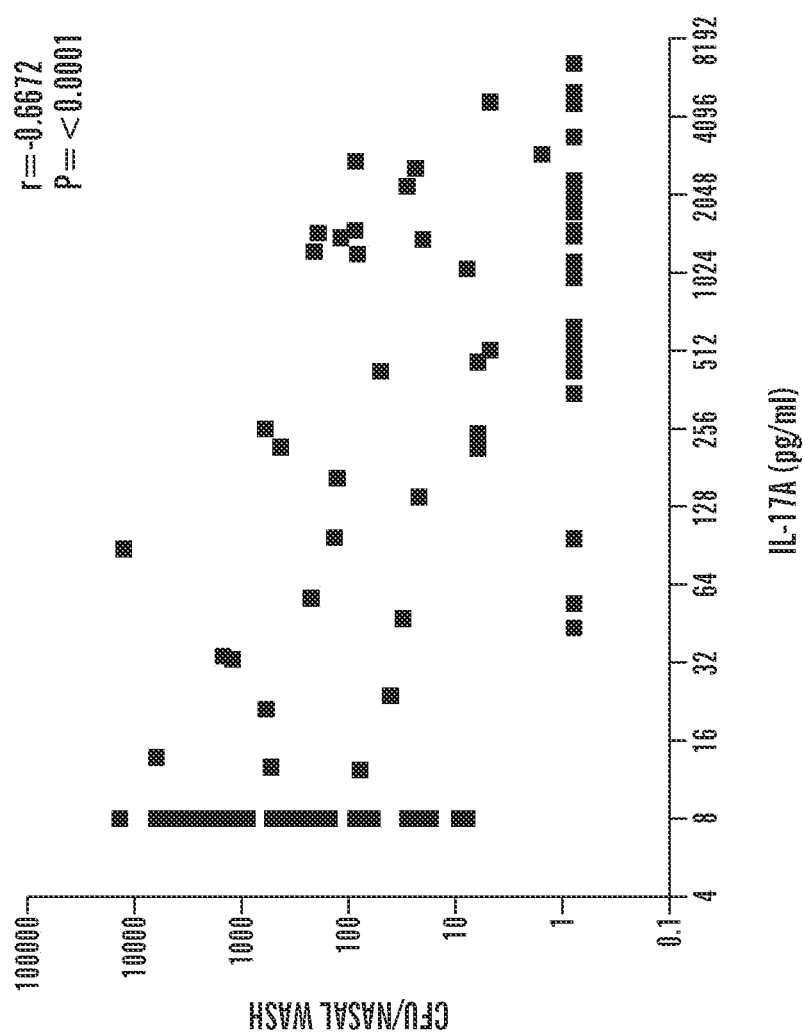
Figure 5C:
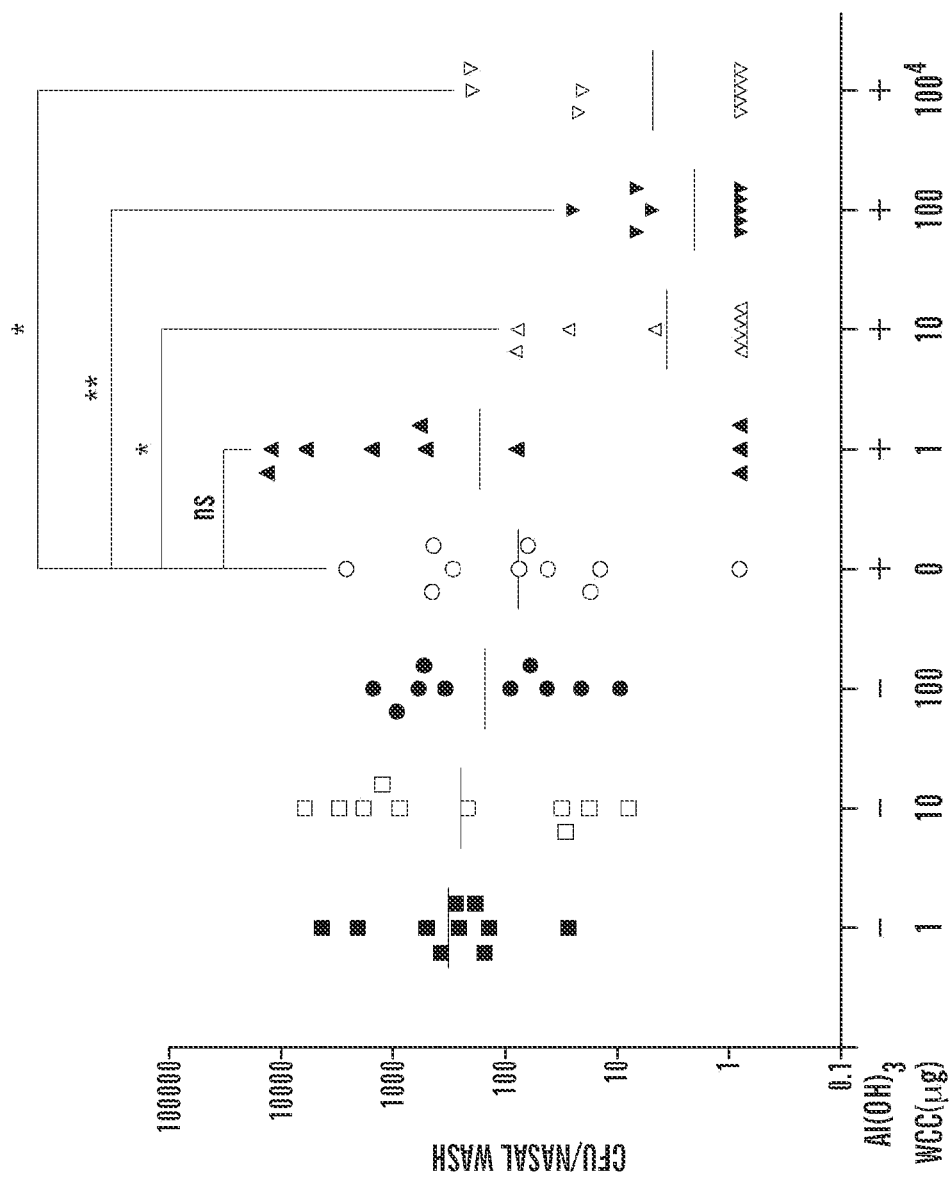

Without adsorption, there was no protection against experimental NP colonization with serotype 6B strain 0603, but with Al(OH)$_3$ the two higher WCC doses gave significant reduction of CFU (FIG. 5C). A similar enhancement by aluminum adjuvant was observed for injected WCB, and protection by adsorbed WCB in the colonization model was correlated with IL-17A priming (FIG. 2A). Adsorbed WCB and WCC were quantitatively compared in IL17A priming and protection in the colonization model: WCC and WCB at doses of 10 μg or 100 μg, adsorbed onto Al(OH)$_3$ were injected. The dose-dependent IL-17A responses did not differ (FIG. 6A). Clearance of serotype 6B from the nasopharynx also was indistinguishable (FIG. 6B). Dependence upon the CD4+ pathway in this model was evaluated in a group of WCC-immunized animals given anti-CD4+ antiserum just prior to challenge to eliminate these cells as effectors of protection; in these mice the protection was eliminated (2nd column, FIG. 6B).

Figure 7A:
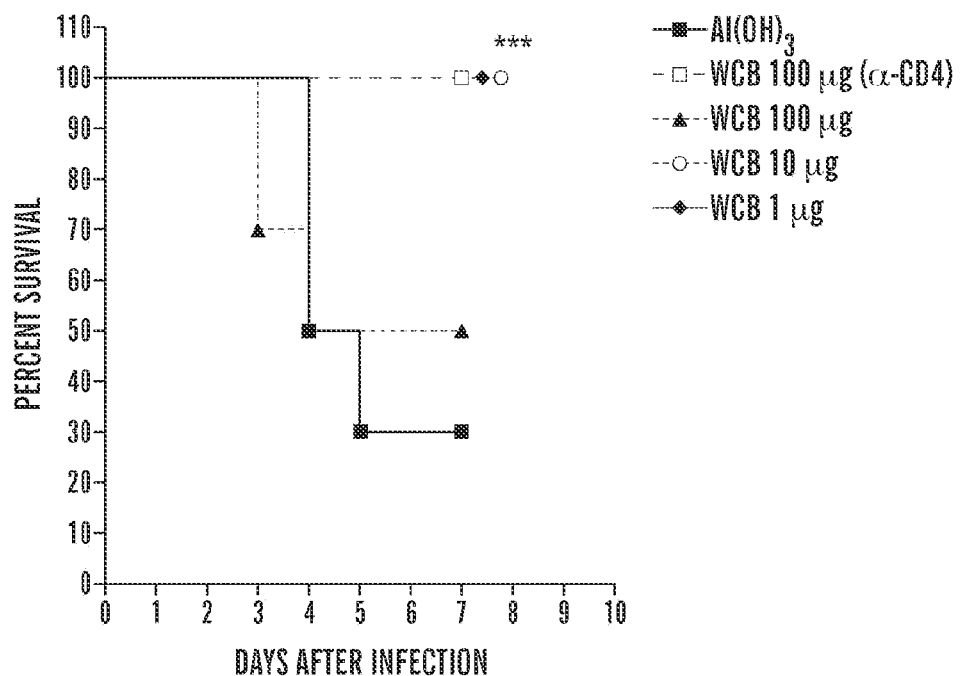
FIGS. 7A-7C show the effect of 3-injection or 2-injection schedules of WCB upon fatal serotype 3 aspiration sepsis. WCB at doses of 1, 10, or 100 μg was adsorbed to $Al(OH)3$ (0.21 mg Al/dose) and given at two-week intervals.

To determine the protection in the model of fatal aspiration-sepsis with serotype 3 strain WU-2 (Lu et al., 2009; Malley et al., 74 Infect. Immun. 2187, 2006), WCB-Al (OH)$_3$ at doses of 1 μg, 10 μg, and 100 μg were thrice injected. Of the controls receiving Al(OH)$_3$ alone, 7/10 mice died (FIG. 7A) and two of the three survivors were bacteremic by the close of the 7-day observation period. There was dose-dependent protection by WCB: half the mice receiving 1 μg and all receiving 10 μg or 100 μg survived the 7-day observation period; none of the surviving vaccinated mice were bacteremic. As expected, there were dose-dependent increases in the IL-17A and antibody responses, and protection in the lethal model was correlated with the pre-challenge antibody titer of individual mice. Protection was uniformly observed when the serum anti-pneumococcal IgG antibody response in mice exceeded 10,000 arbitrary units (FIG. 2B).

Figure 7B:
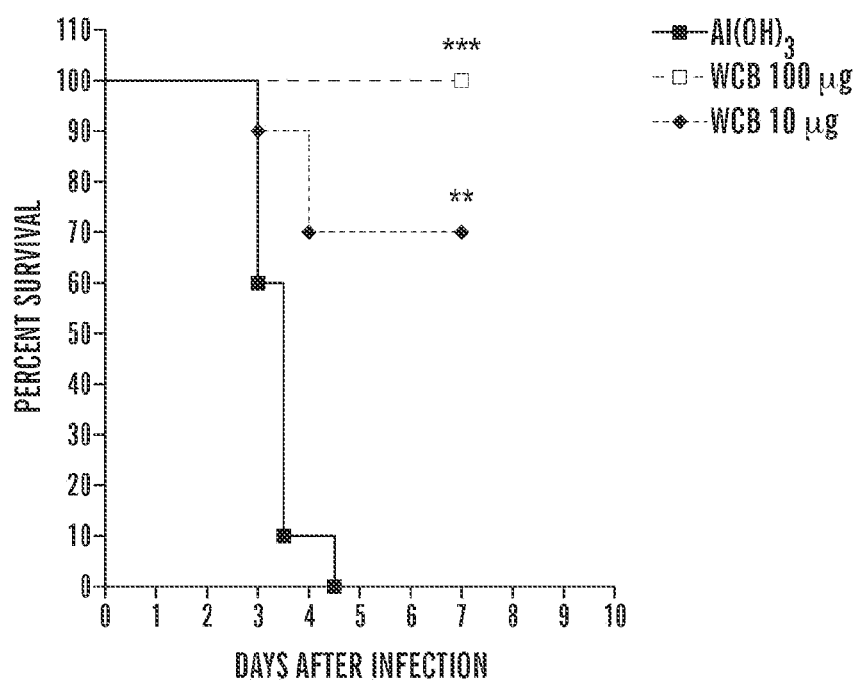
Figure 7C:
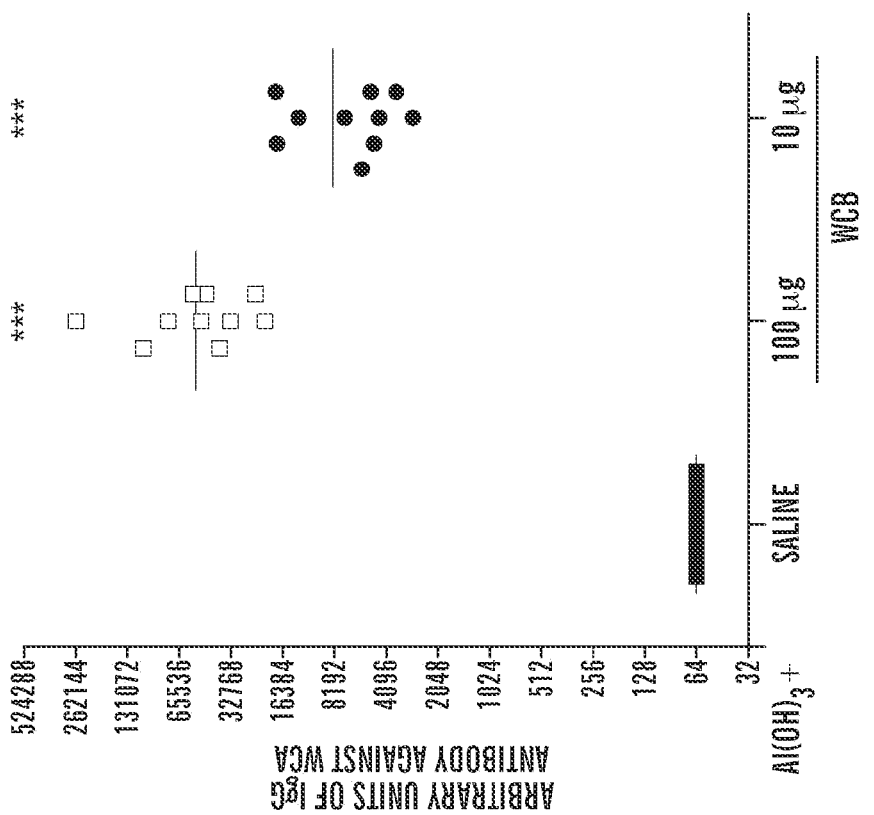

Protection in this model was tested also with just two injections. Doses of 10 μg or 100 μg were given 2 weeks apart, followed by blood sampling one week later and challenge 2 days thereafter. The 10 μg dosage was partially and the 100 μg dose completely protective against death or bacteremia (FIG. 7B); the serum IgG antibody response in the 2 injection schedule was substantial; titers were about 7-folder greater after the higher dose (FIG. 7C). When adsorbed WCB was administered by intramuscular injection, protection in the lethal challenge model was observed likewise. Currently, this is a routine route for injection of vaccines into humans.

Routinely, adsorption was done for 18 hours to 22 hours at 4° C., and the preparations were tested immediately. To test the stability of the adsorbed antigen, Al(OH)$_3$ with WCC at 100 μg per dose was incubated at 37° C. for 1 month before testing in the above-described experiment. The IL-17A responses, antibody titers and protection results did not differ from the same dosage of freshly prepared WCC-Al(OH)$_3$ (FIGS. 5A, 5B, 5C, last column, indicated by the Δ superscript). Thus there is stability as a liquid suspension, an advantage for injectable vaccines.

Although the protection by injected WCB against lethal intranasal challenge correlates with the IL17A assay as well as with the antibody response, depletion of CD4+ T cells in this model (thereby significantly impairing the IL-17A response) does not block the protection. Thus a necessary function of antibody is implied. As noted above, protection of individual mice correlates with their pre-challenge titer of antibody to the whole-cell antigen (FIG. 2B). An indication of the functional role of antibody in this model is shown by passive protection with heat-inactivated serum from WCB-vaccinated rabbits, as will be illustrated below (FIG. 8B).

Figure 4A:
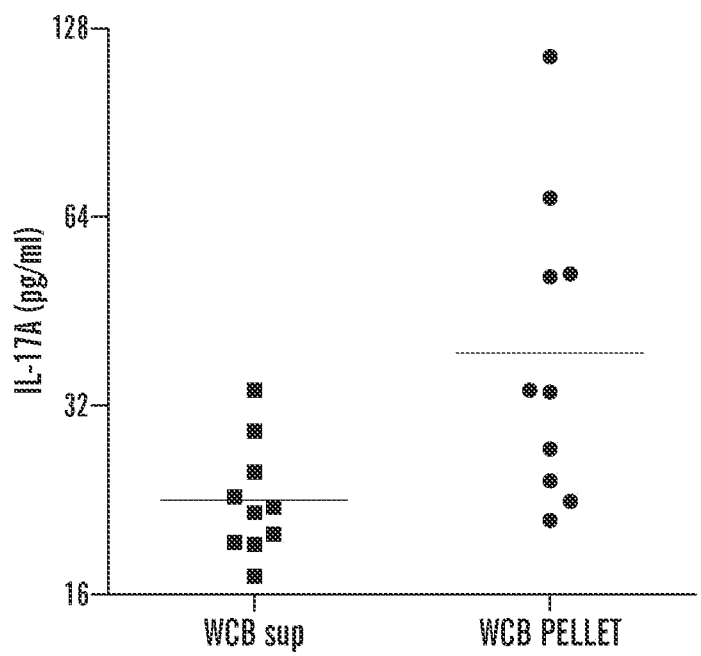
FIGS. 4A and 4B show priming for IL-17A responses to WCA (FIG. 4A) and antibody response to WC antigen (FIG. 4B) induced by WCB supernatant or pellet (cellular) fraction. The supernatant (WCBsup) was prepared by centrifuging at 16,000×g for 30 min. Antigens were absorbed to $Al(OH)_3$ (0.24 mg Al/dose). Each mouse received a 30 μg dose (protein content) per immunization. Mice were immunized twice at a 2-week interval, and blood samples for the assays taken 1 week after the second immunization. The cellular fraction was more potent in eliciting IL17A responsiveness, while the supernatant was as potent or more so in eliciting antibody.
Figure 4B:
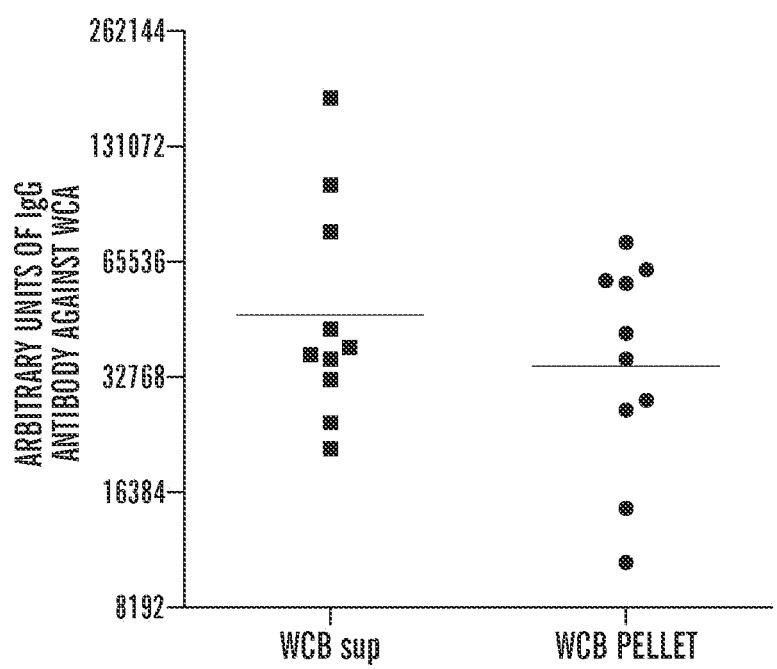

Thus, the use of two different models of infection shows that the pneumococcal whole-cell vaccine has the potential of a two-pronged immunity: protection against nonlethal colonization, dependent upon IL17A, and against lethal invasion, mainly dependent upon antibody. The two-pronged immunity is facilitated by the vaccine's containing both cellular and soluble components. In the experiment shown in FIGS. 4A-4B, a sample of WCB was centrifuged to produce cellular ("pellet") and soluble ("sup") fractions. Equal amounts [30 μgrams by protein content] of the fractions were injected. FIG. 4A shows that the cellular fraction is superior for priming for the IL-17A response, and FIG. 4B shows the soluble fraction is equal or better for the antibody response. Thus, inactivation of the vaccine bacteria with agents that selectively disrupt the cells to release protective antigens, but that do not require subsequent removal of the soluble phase, constitutes a simple procedure to generate vaccines providing a two-pronged protective response.

Figure 1D:
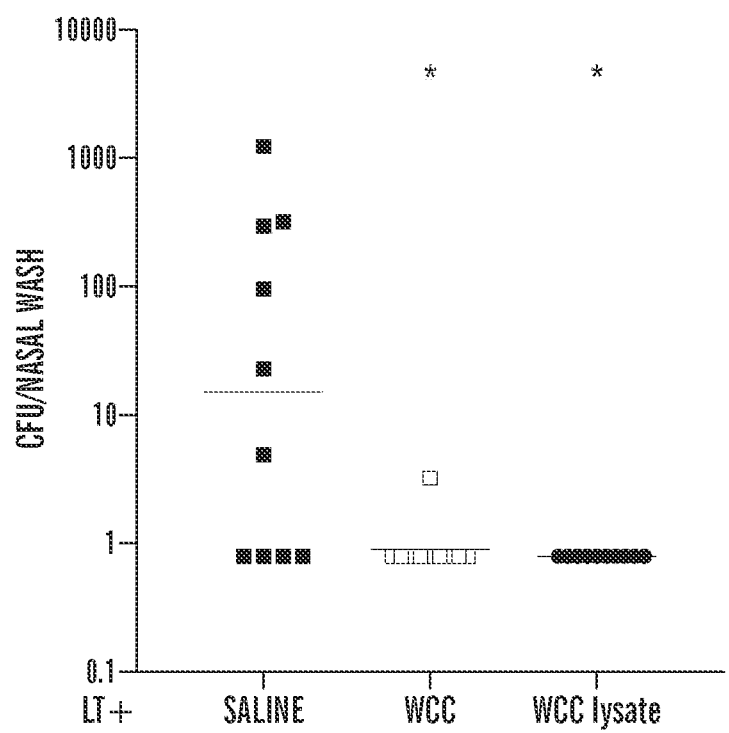
FIG. 1D shows that the lysate was comparably protective.
Figure 1E:
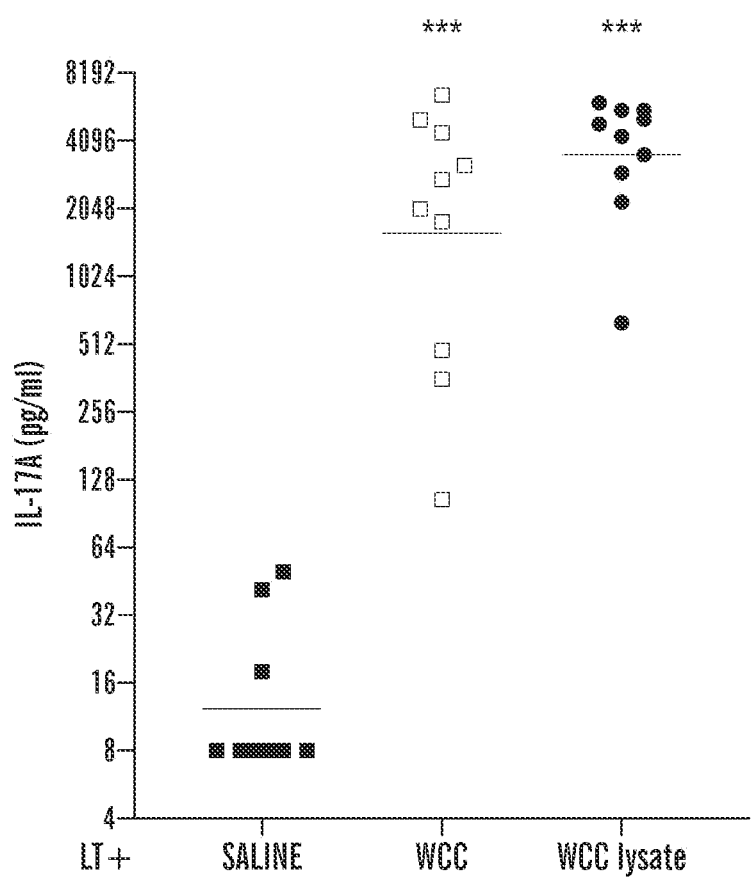
FIG. 1E shows it to have comparably primed for IL-17A responses by blood cells in vitro, a correlate of protection in the colonization model.

Another embodiment of the present invention provides for protection by an ultrasonically solubilized preparation. Extending the observation of protection by soluble components, a sample of WCC was sonicated to disrupt the cells, and this lysate was compared to the corresponding dosage of intact WCC. FIG. 1D shows that the lysate was comparably protective, and FIG. 1E shows it to have comparably primed for IL-17A responses by blood cells in vitro, a correlate of protection in the colonization model. Lu et al., 2008.

As a general approach, dosage of WCA can be quoted in μg of protein, of which about 85% is cellular and ca 15% is soluble (Lu et al., 2010); 1 μg corresponds approximately to a total dry weight of 1.7 μg and to $10^6$ CFU before killing. For active immunization of mice, two or three sequential injections were given two weeks apart, blood was taken I or 2 weeks after the last injection for assays of priming for IL-17A expression in vitro and of serum IgG antibody to WCA, the animals were challenged with pneumococcus in either the colonization model or the aspiration-sepsis model, and the outcome in individual mice compared to the in vitro assay values.

To demonstrate expanded serotype coverage, the aspiration-sepsis challenge of mice was induced with a pneumococcal serotype not previously used: challenge with type 5 strain DBL5 was fatal with as little as $10^5$ CFU/aspiration. The 2-injection sequence with 100 μg doses of WCB Al(OH)$_3$ was tested and found highly protective against challenges with $10^5$ or $10^7$ CFU/aspiration.

Preliminary toxicology assessment and immunogenicity were assessed in rabbits. New Zealand White females in groups of 3 were injected intramuscularly on day 1, 15, 29 and 43 with saline, Al(OH)$_3$ alone (0.21 mg of Al), Al(OH)$_3$-adsorbed WCB at doses of 50, 500 or 5000 or—as a known toxicity control—a commercial DTwP vaccine. No test article-related clinical signs, dermal irritation, loss of appetite or temperature changes were observed throughout.

Upon necropsy, there were no definitive test article-related macroscopic findings in any of the groups in this study.

Although not clearly dose-dependent, neutrophils and monocytes showed mild to moderate increases (1.58 to 1.87-fold relative to alum adjuvant) in all WCB groups. Fibrinogen increased dose-dependently and progressively from day 2 (1.16- to 1.94-fold relative to alum adjuvant) to day 45 (1.31- to 2.62-fold relative to alum adjuvant) in animals receiving the mid- and high-WCB doses. Globulins were mildly elevated in the groups that received WCB 500 μg and WCB 5,000 μg. Changes in these clinical pathology parameters are consistent with an inflammatory response to the vaccine. Numerous microscopic findings were seen in the intramuscular injection sites, with findings varying between the different control groups and the WCB test article injections. These findings were generally greatest for injection site 4 (day 45) and showed ongoing recovery over time (injection site 1, day 1). The only slight evidence of dose dependence between the WCB immunized groups was seen in the finding of subcutaneous hemorrhage/inflammation/necrosis.

Overall, findings of muscle and subcutaneous inflammation were increased to some degree in all of the WCB groups compared to the Group 2 controls, with no consistent evidence of dose dependence for either severity or incidence of any of these findings across all injection sites. WCB groups, as a whole, did not consistently have increased incidence or severity of any microscopic findings compared to the DTwP controls.

To summarize, WCB was examined at three dose levels, 50 μg, 500 μg, or 5,000 μg. Based upon findings limited to inflammation (fibrinogen and microscopic pathology), the no observed adverse effect level (NOAEL) of this study was 50 μg/animal of WCB adsorbed to aluminum hydroxide.

Figure 8A:
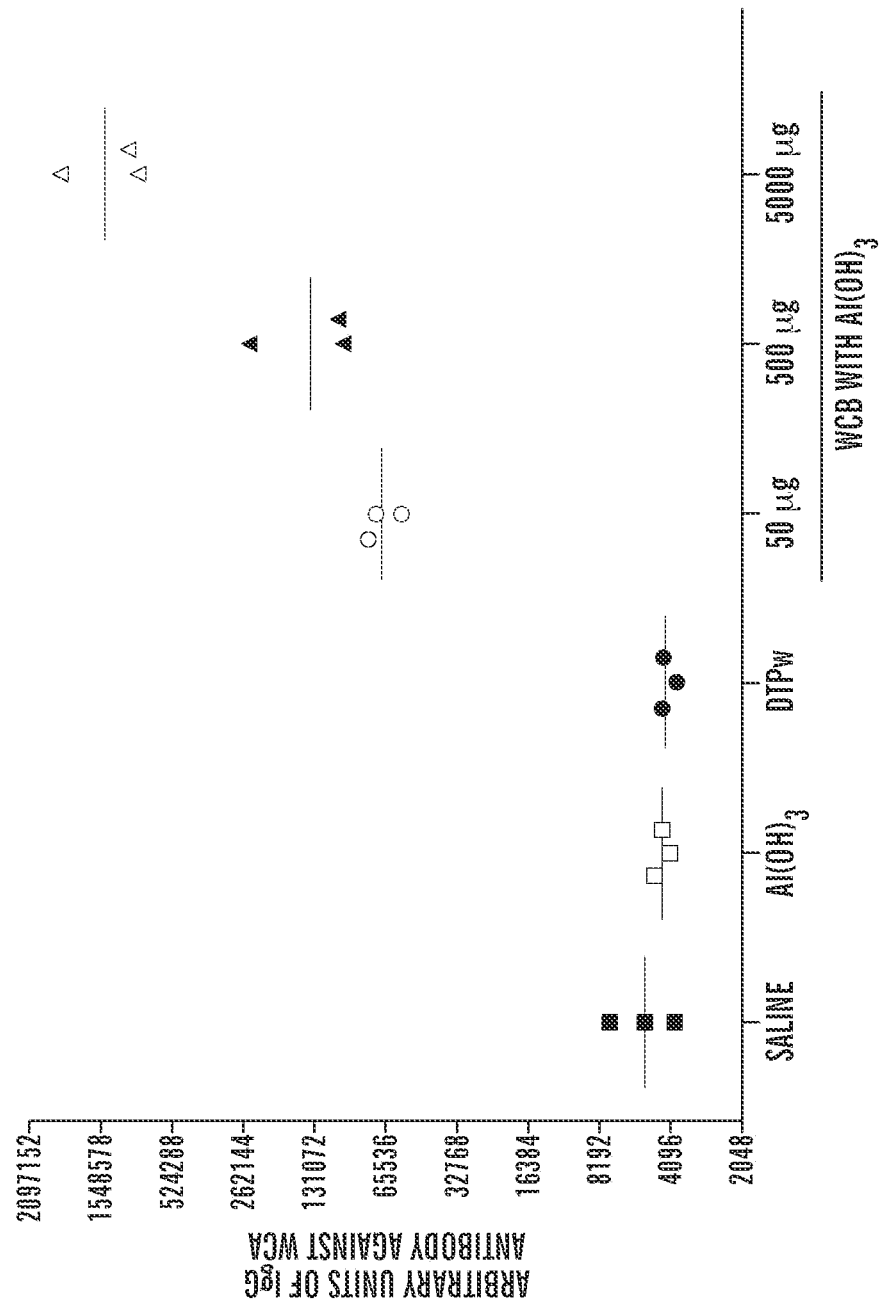
FIGS. 8A-8C show results from rabbit immunization studies. Female New Zealand White animals in groups of three were given, intramuscularly, saline, $Al(OH)_3$ alone (0.6 mg of Al), $Al(OH)_3$-adsorbed WCB at doses of 50 μg, 500 μg or 5000 μg, or DTwP vaccine (a toxicity control) on days 1, 15, and 29. Sera were taken before immunization and at day 43.
Figure 8C:
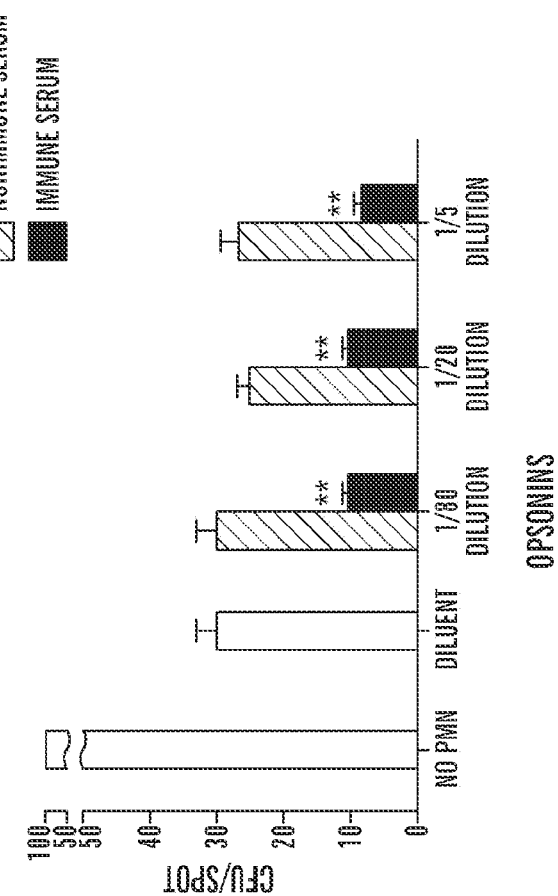
Figure 8B:
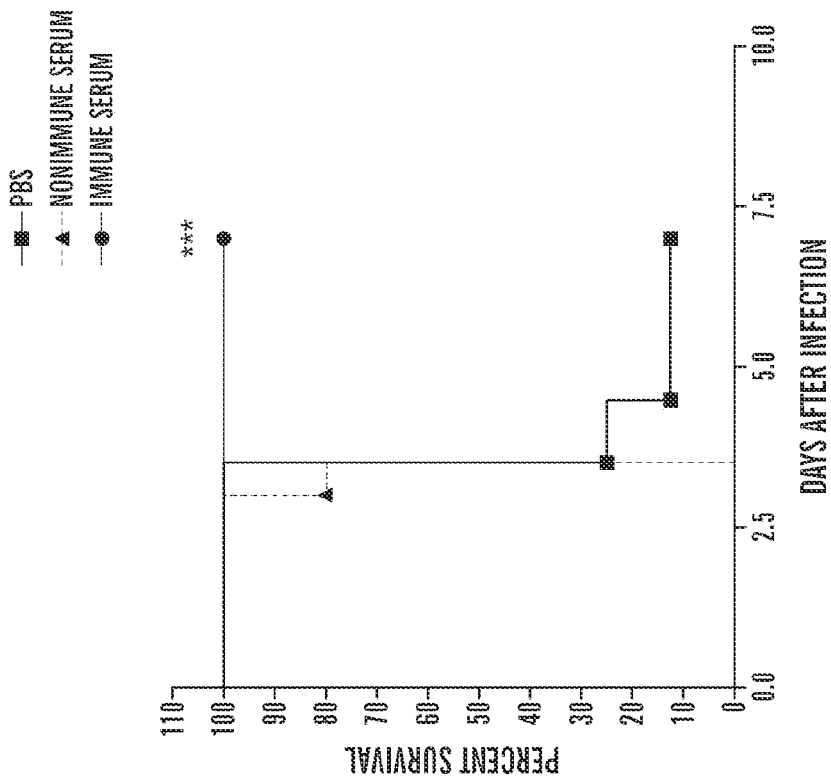

Serum IgG antibody titers in the WCB-immunized rabbits rose progressively and with dose-dependency in samples taken pre-injection on days 1, 15, 29, and 43; the day-43 titers are shown in FIG. 8A. Pools of the day-45 sera from alum and WCB immunized rabbits were tested for passive protection in the mouse aspiration-sepsis model with serotype 3: the day-45 pool was highly protective (FIG. 8B). Heat-treated terminal bleed sera from rabbits that had been immunised with 500 μg of Al(OH)$_3$-adsorbed WCB or alum alone was evaluated in a surface killing assay as described previously. Lu et al., 9 PLoS Pathog e1000159 (2008); Weinberger et al., 5 PLoS Pathog. e1000476 (2009). As shown in FIG. 8C, at the three dilutions tested, immune sera from rabbits significantly enhanced killing of a strain of type 6B pneumococcus by human neutrophils compared to pre-immune sera, indicating that immunization with adsorbed WCB induces opsonophagocytic antibodies.

Figure 15:
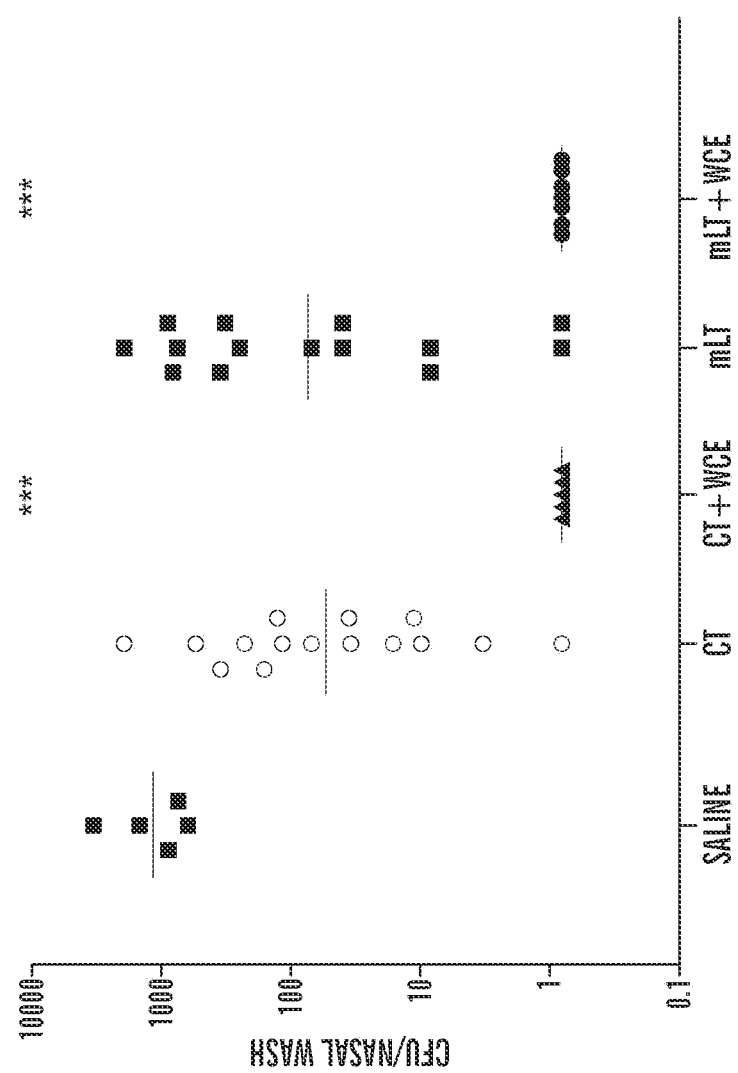
FIG. 15 shows that, compared to saline, the adjuvants given alone gave a suggestion (albeit not statistically significant) of accelerated pneumococcal clearance, an expected result in this model where vaccination and challenge are by the same route. When given with $10^8$ of WCE, however, mLT, like provides excellent protection.

Another embodiment of the present invention provides for protection by WC antigen given intranasally with a nontoxic enterotoxin derivative. Neither CT nor E. coli heat-labile toxin (LT) is suitable for intranasal human use, which prompted the evaluation of nontoxic mutants of LT. A singly mutated derivative of E. coli heat-labile toxin (mLT, R192G) was compared to CT. FIG. 15 shows that, compared to saline, the adjuvants given alone gave a suggestion (albeit not statistically significant) of accelerated pneumococcal clearance, an expected result in this model where vaccination and challenge are by the same route. When given with $10^8$ of WCE, however, mLT, like provides excellent protection.

Figure 10A:
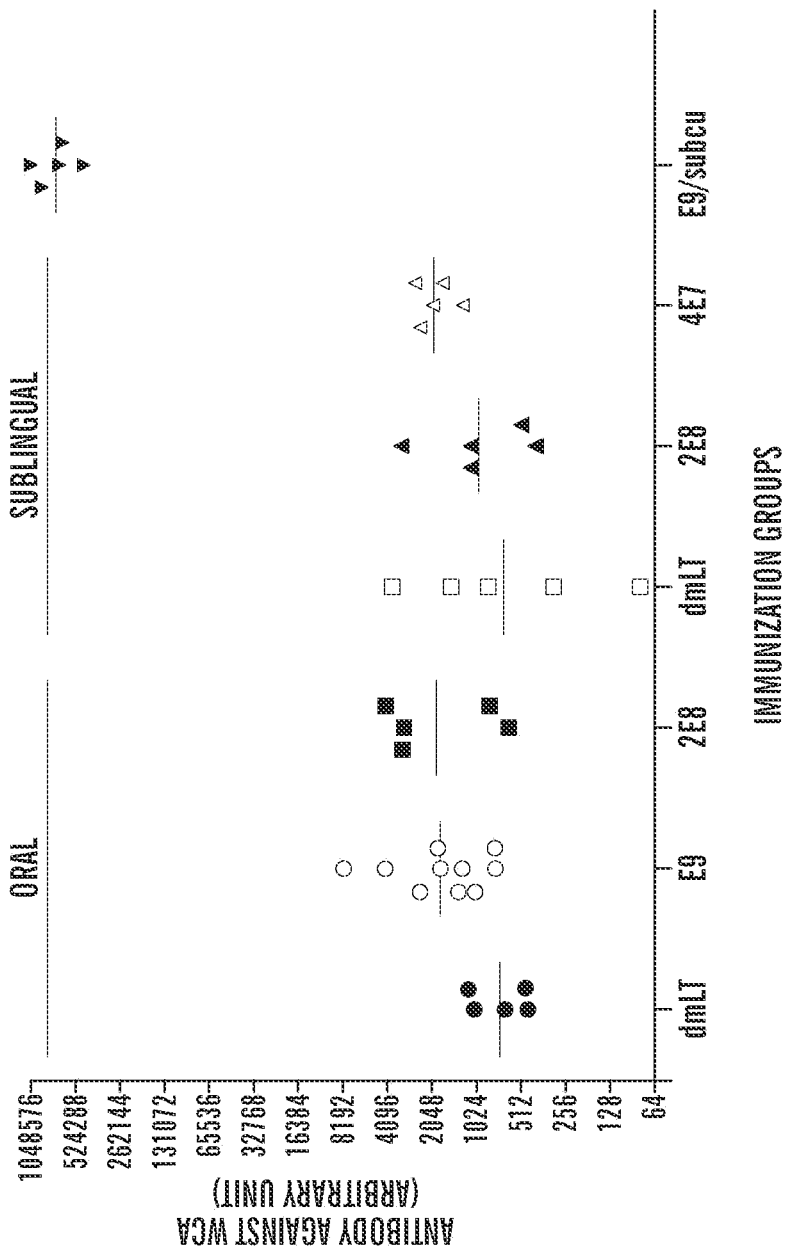
FIGS. 10A-10B show the immunogenicity of WCC antigen at the indicated doses (in viable cell count prior to killing) by the buccal and sublingual routes, tested with 10 μg of doubly mutated LT adjuvant, R192G/L211A (dmLT). These immunizations were given thrice with weekly intervals. Challenge was as described for FIG. 2.
Figure 10B:
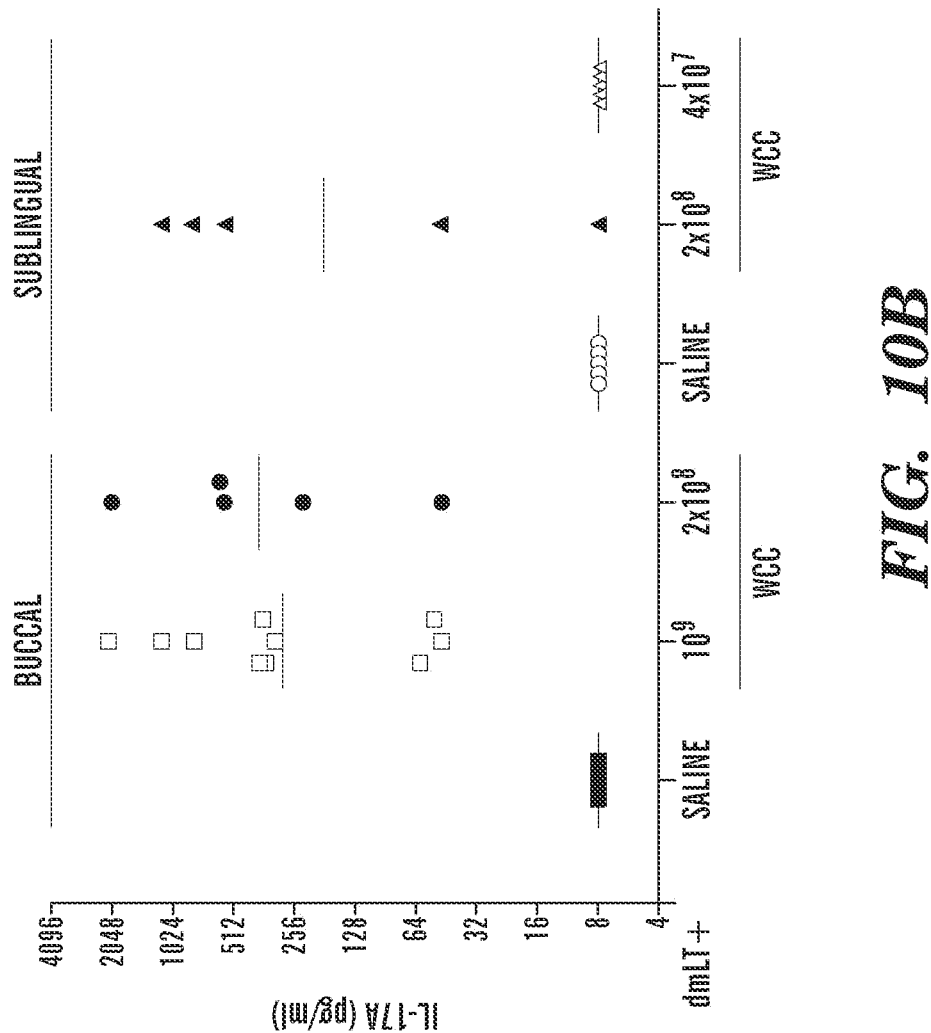
Figure 11A:
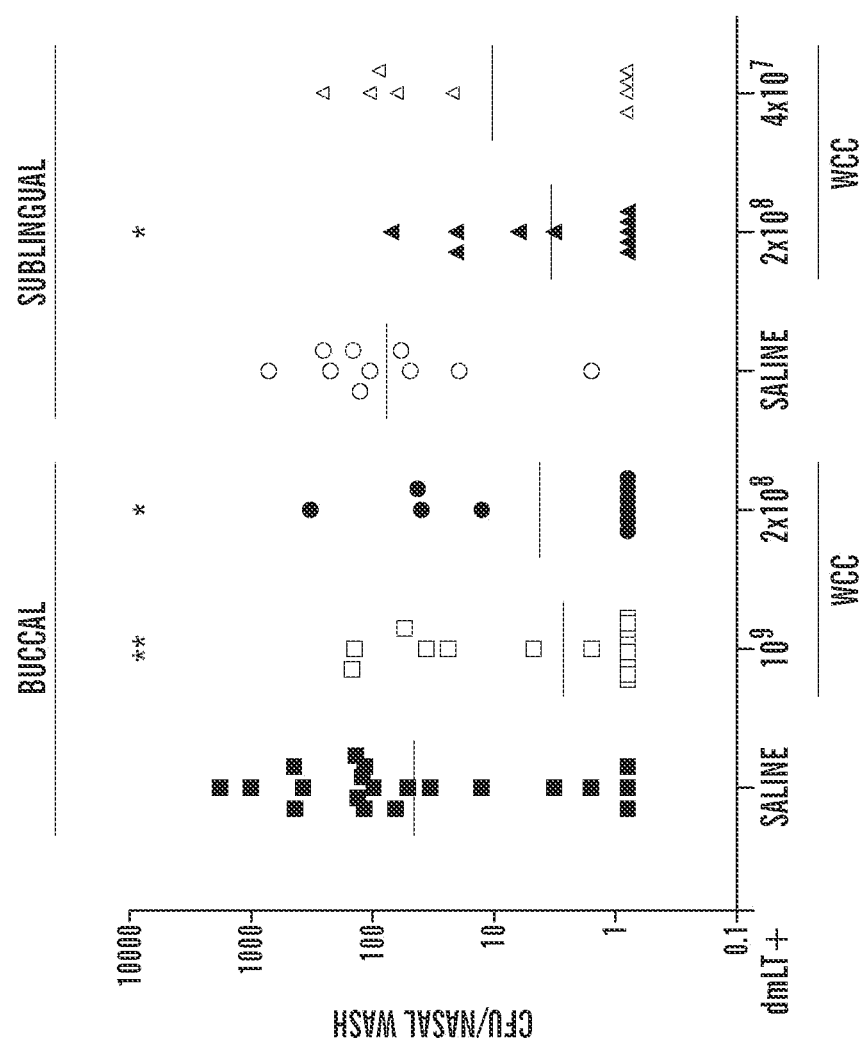
FIG. 11A shows that both buccal and sublingual routes induced a dose-dependent enhanced clearance of serotype 6B from the nasopharynx.

Additionally, the present invention provides for immunogenic preparations suitable for administration by the buccal and sublingual routes. Recent reports raised concern over the safety of E. coli heat-labile toxin (LT) and even detoxified mutants of LT when given by the intranasal route and pointed to a possible association between their use and the development of Bell's palsy. Lewis et al., 4 PLoS one e6999 (2009); Mutsch et al., 2004. Another drawback of intranasal vaccination in infancy is that in subjects presenting with copious nasal mucus, frequent in some clinical settings, effective contact of the vaccine with the mucosa would be compromised. Therefore, alternative mucosal routes were tested: application to the buccal mucosa along side the lower molars (frequently used for live polio vaccination of children) and sublingual application, a route recently analyzed cytologically in detail. Cuburu et al., 183 J. Immunol. 7851 (2009). Both routes give access to the immunoresponsive tissues of Waldeyer's ring with less access to the central nervous system and circumvent the problem of nasal mucus. The buccal and sublingual routes were explored using WCC and a doubly mutated LT (dmLT, R192G/L211A) as an adjuvant. Dose-dependent protection was found with both routes of administration (FIG. 11A). Consistent with the protection, priming for IL-17A responses in vitro was observed (FIG. 10B).

Figure 12A:
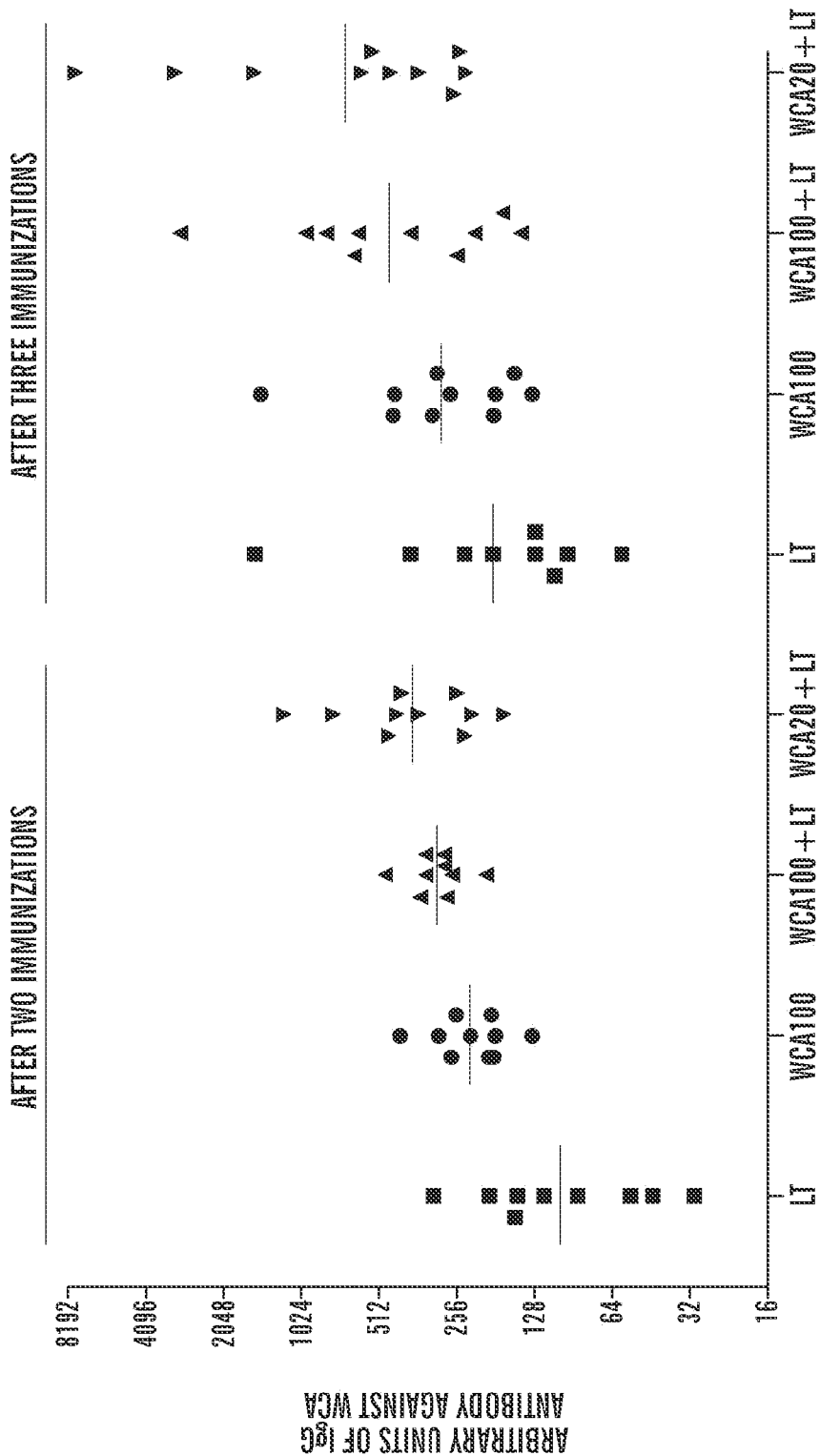
FIGS. 12A and 12B present immunogenicity data (IgG vs. WCA and IL-17A) when WCC is given with *E. coli* heat-labile toxin (LT).
Figure 12B:
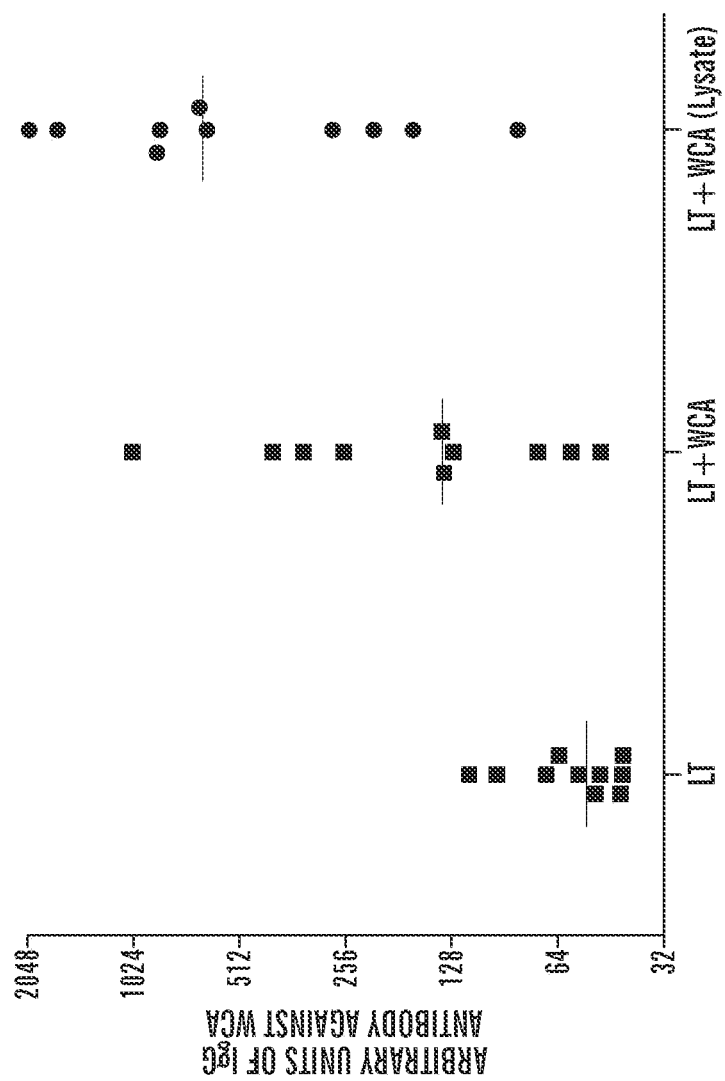
Figure 12C:
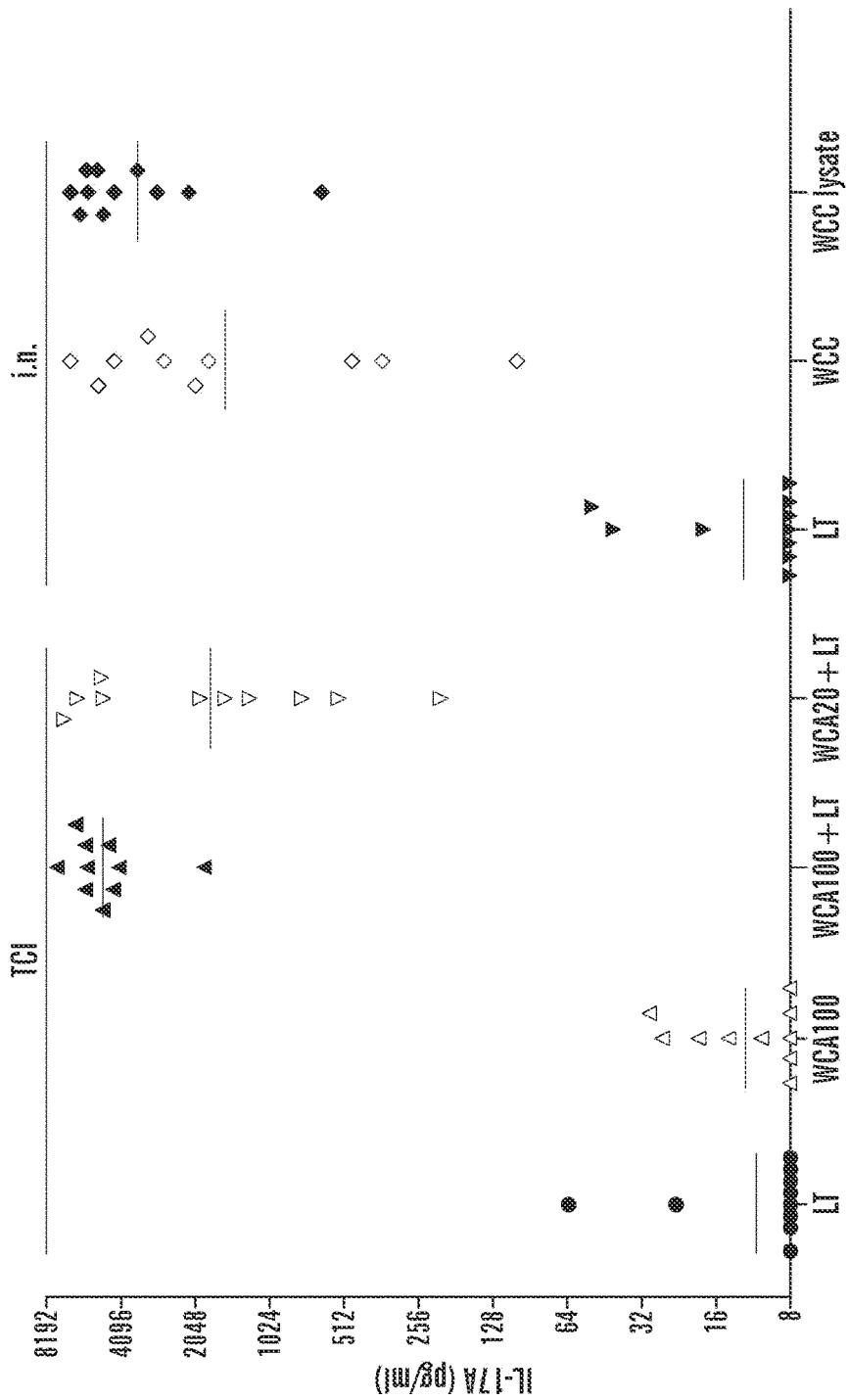
FIGS. 12C and 12D show immunogenicity by the transcutaneous route (TCI) of ultrasonically produced fragments of WCC. Fragments with a mean diameter of 100 or 20 nm in dosage equivalent to $10^8$ cells were applied, along with 1 μg of LT adjuvant where indicated, in cotton gauze patches onto dorsal skin gently abraded to remove the stratum corneum. The patch was left in place for 18 hr. This immunization was given thrice with a 2-week interval. Blood samples were taken 10 days after the third immunization for assays of IL-17A, and pneumococcal challenge was done 6 days later.
Figure 12D:
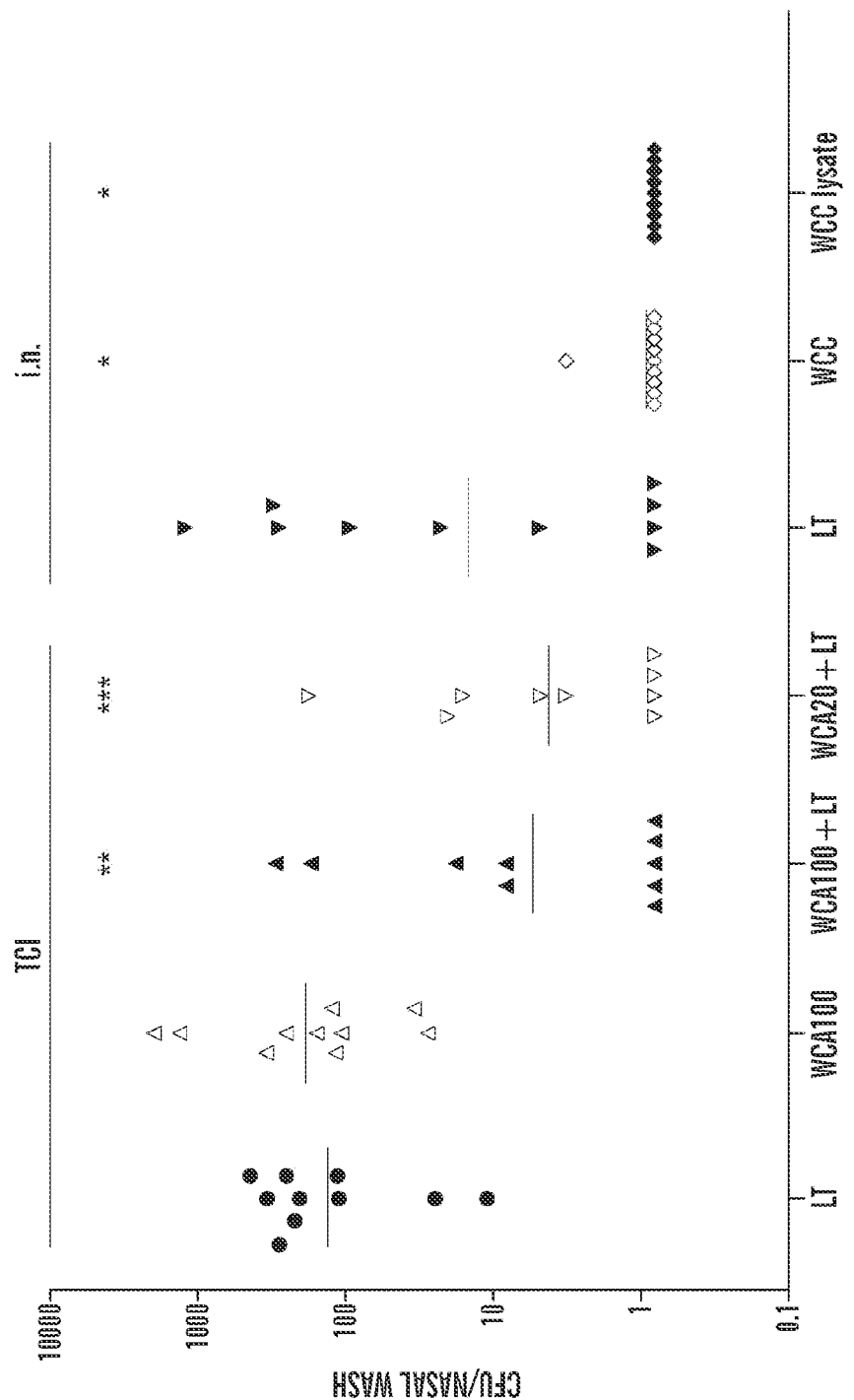
Figure 13A:
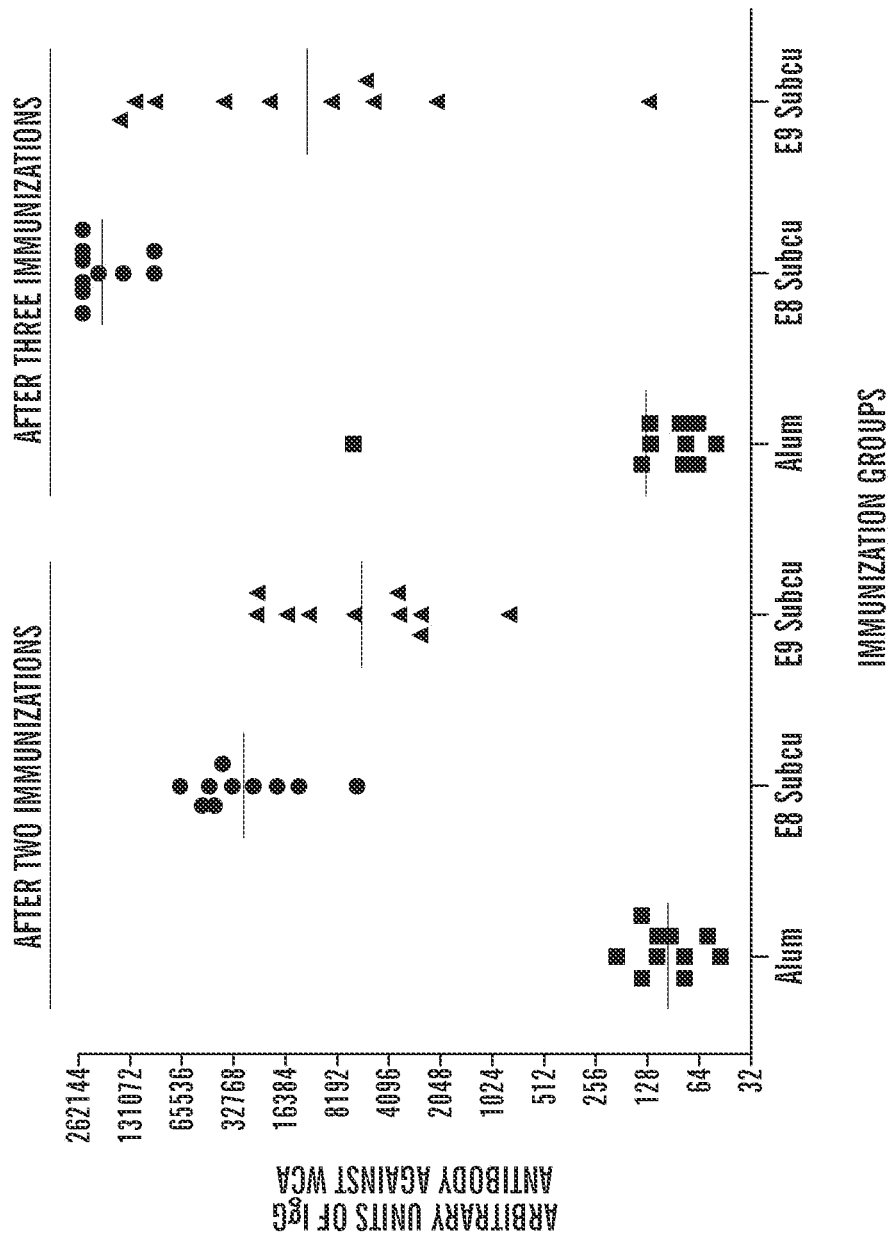
FIGS. 13A-13C show the relationship between number and dosages of immunization and antibody responses (FIG. 13A), IL-17A responses (FIG. 13B), and colonization (FIG. 13C).
Figure 13B:
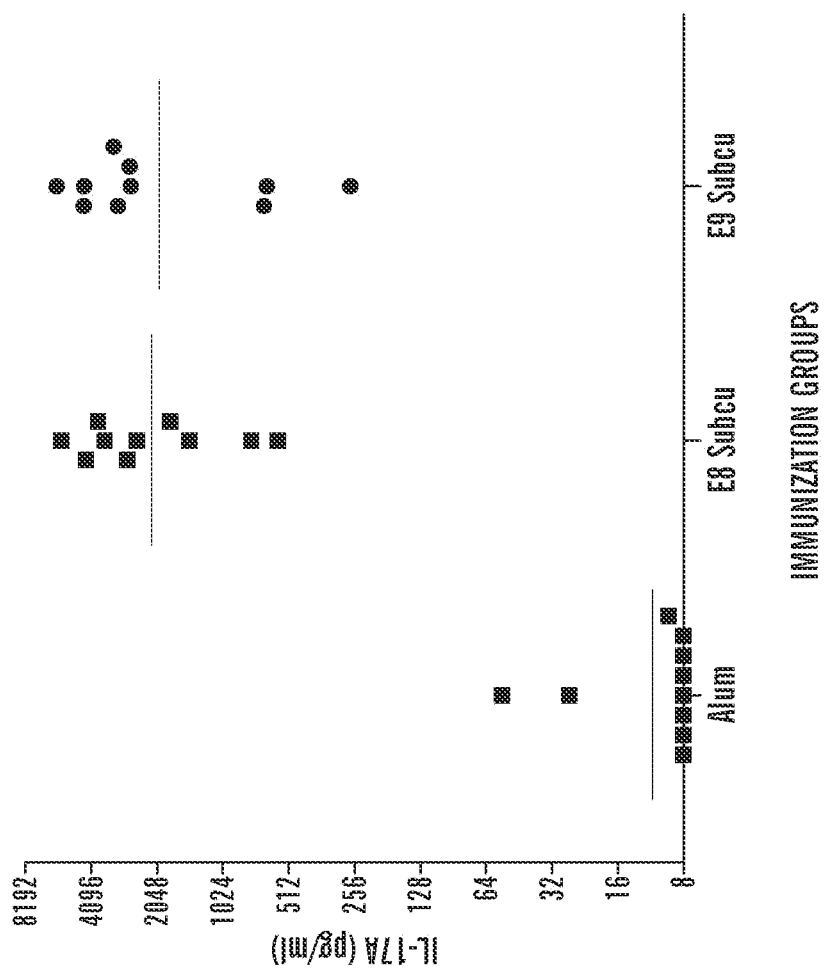
Figure 13C:
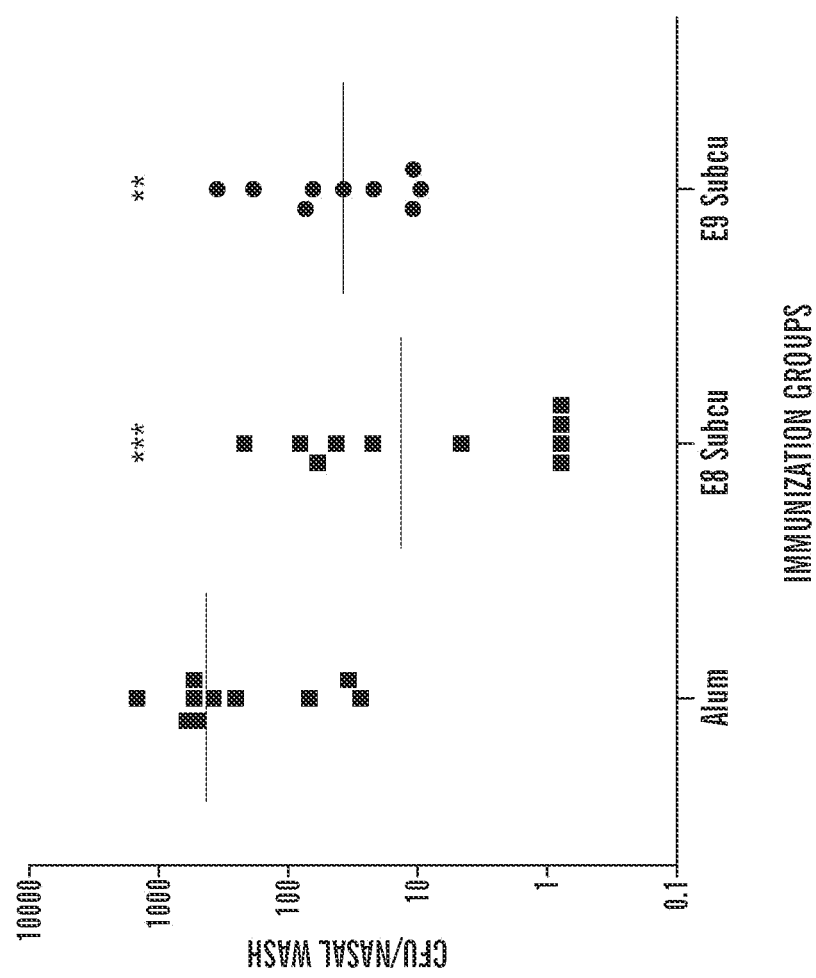

The present invention also provides for immunogenic compositions administered by transcutaneous immunization (TCI) with ultrasonically produced fragments of WCC. The transcutaneous immunization route was tested by application of cotton gauze patches containing antigen and LT adjuvant to the dorsal skin lightly abraded to disrupt the stratum corneum as done previously for other vaccine preparations. Zhu et al., 15 Clin. Vaccine Immunol. 359 (2008). Experience with other systems commended reduction of particle size, so fragments with mean diameters of 100 nm (WCC100) and 20 nm (WCC20) were tested. WCC100 and WCC20 were similarly protective when applied with LT, in comparison with LT or with WCC100 applied alone. Consistent with the protection, priming for IL-17A responses in vitro greatly exceeded levels associated with protection by i.n. immunization (FIG. 12C). See also Lu et al., 2008. Transdermal vaccination thus is another alternative to the intranasal route.

Pneumococcal capsular polysaccharide-protein conjugate vaccine has been effective against systemic disease in infancy for the included serotypes and has provided some herd immunity. Hsu et al., 360 N. Engl. J. Med. 244 (2009); Lexau et al., 294 JAMA 2043 (2005); Whitney et al., 348 N. Engl. J. Med. 1737 (2003). The complexity of manufacture, relative high cost of production, and increasing serotype replacement disease (Hanage, 2008) have led to efforts to develop a serotype-independent and more economical vaccine. These include purified protein antigens (Basset et al., 75 Infect. Immun. 5460 (2007); Briles et al., 18 Vaccine 1707 (2000); Giefing et al., 205 J. Med. Exp. 117 (2008); Glover et al., 76 Infect. Immun. 2767 (2008)), and vectored protein antigens (Arevalo et al., 55 FEMS Immunol. Med. Micro. 346 (2009); Kong et al., 105 PNAS 9361 (2008); Li et al., 106 PNAS 593 (2009); Nayak et al., 66 Infect. Immun. 3744 (1998); Xin et al., 77 Infect. Immun. 4518 (2009)), as well as the noncapsulated WCV studied here (Lu et al., 2008; Malley et al., 2003; Malley et al., 72 Infect. Immun. 4290 (2004)), each of which may be used in combination with the immunogenic compositions of the present embodiments.]

Carriage always precedes pneumococcal disease (Austrian, 1986), so the vaccine-induced enhanced clearance of carriage (Lu et al., 2008) may be protective against pneumonia and invasive disease. The present embodiments provide for immunogenic compositions that reduce the duration and intensity, but not necessarily eliminate carriage. For example, in mice, WCV does not block colonization, but rather accelerates clearance from the nasopharynx (Bogaert et al., 77 Infect. Immun. 1613 (2009); Lu et al., 2008; Malley et al., 2001; Malley et al., 2004; Malley et al., 2005.

Although the killed WC antigen, an array of many different antigens, present in both particulate and soluble forms, has potential challenges regarding manufacturing consistency and standardization, its potency, low cost of production, stability as a lyophile, and possible administration without syringes make it worthy of clinical development.

For such a complex antigen, straightforward standardization and quality control by biochemical criteria is not feasible. A potency assay based upon animal immunization is required; but animal challenge tests as an endpoint are not ideal, and correlates determined by in vitro assay are preferable. Priming of mice for generation of IL-17A in vitro is a correlate of protection by WCV given by many routes (Lu et al., 2010), but this assay requires tissue culture facilities that may not be readily available in many developing countries. As shown herein, when WCV was given s.c. serum IgG antibody to WCA determined by ELISA is both a correlate and an agent of protection against invasive disease. Therefore, the planned initial clinical evaluation of WCV is as an aluminum adsorbed antigen for intramuscular injection, and the primary potency criterion will be by mouse immunization and ELISA for IgG antibody after two sequential injections. The IL-17A assay could potentially serve as a supplementary criterion. Like the IgG ELISA, the IL-17A assay can be conducted with small samples of human blood, so both would be useful biomarkers in clinical trials.

The success of the 7-valent pneumococcal conjugate vaccine (PCV) against invasive disease in the US and the results from clinical trials in South Africa and The Gambia of a 9-valent PCV (Klugman et al., 349 N. Engl. J. Med. 1341 (2003); Cutts et al., 365 Lancet 1139 (2005)), understandably led to the inference that, given enough serotype coverage with future generation conjugate vaccines and lowering of cost, pneumococcal disease could be significantly controlled, if not eradicated, in both developed and developing countries. The recent licensure in Europe and the US, respectively, of so-called "second generation" 10- and 13-valent pneumococcal vaccines represent further important advances in this area. The emergence of serotypes not included in the first generation 7-valent conjugate vaccine, however (Hanage, 3 Future Microbio. 23 (2008)), and the demonstration that these strains are important causes of disease, morbidity and mortality (Singleton et al., 297 JAMA 784 (2007); Hsu et al., 369 N. Engl. J. Med. 244 (2009)), is a cause for concern. Although current efforts to promote the use of appropriately broad pneumococcal conjugate vaccines in developed and developing countries are continuing, the need for alternative approaches to vaccination against pneumococcus remains a priority.

Over the past decade, several research groups have focused on the development of species-specific pneumococcal vaccines that would lead to clinical trials. Nabors et al., 18 Vaccine 1743 (2000); Briles et al., 182 J. Infect. Dis. 1694 (2000); Giefmg et al., 205 J. Exp. Med. 117 (2008); Oliveira et al., 8 Microbes Infect. 1016 (2006); Ogunniyi et al., 68 Infect. Immun. 3028 (2000). It is nevertheless sobering that, to date, no such vaccine has progressed to Phase III clinical trials. Furthermore, it is clear that the development of a species-specific pneumococcal vaccine faces several important hurdles for development and licensure, including, but not limited to, the choice of study population, endpoints and ascertainment of efficacy, comparisons to the currently-approved conjugate pneumococcal vaccines, route of administration and potential need for adjuvants for optimal stimulation of mucosal immunity.

In a particular embodiment, strain RM200 was used to make WC antigens. In strain Rx1E, to improve yield by reducing autolysis, the entire lytA genomic coding region was replaced by the Janus cassette marked with kanamycin resistance gene rpsL. Sung et al., 67 Appl. Environ. Micro. 5190 (2001); Trzcinski et al., 69 Appl. Environ. Micro. 7364 (2003). An integrant that displayed the correct lytA::Janus genomic context, was resistant to deoxycholate lysis, and had growth kinetics similar to those of the wild-type strain was designated RM200. Rx1E expresses PdT, a nonhemolytic derivative of pneumolysin (Berry et al., 1995), which is both a toxin and protective antigen. To ascertain retention of PdT expression, RM200 was tested for hemolytic activity with sheep erythrocytes, standardized with the purified pneumolysin protein, and found to be nonhemolytic with as many as $5 \times 10^8$ cells, whereas 100-fold fewer pneumolysin-expressing whole cells induce full lysis in erythrocytes ($8 \times 10^6$ and $5 \times 10^5$ cells of pneumolysin-expressing WCE and WCC, respectively); the pneumolysin lower limit of detection of the assay is 0.05 ng/ml. Western blot analysis with anti-pneumolysin serum confirmed that the PdT protein was expressed.

The techniques presented herein, for preparing whole-cell immunogens using selective disruption and the retention of the released soluble fraction, may be useful for vaccine preparation in other gram-positive bacteria, for example Streptococcis (including Group A and Group B *Streptococcus*), Enterococci (including *faecalis* and *faecium*), *Staphylococcus aureus* or nonaureus, *Enterococcus*, *Bacillus* (including *Bacillus anthracis*, the causative agent of anthrax), *Clostridium*, *Corynebacterium*, *Nocardia*, *Mycobacteria* (including *M. tuberculosis*, nontuberculosis *mycobacteria*, *M. leprae*) and *Listeria*.

Further, other bacterial antigenic components may be combined with the present immunogenic composition, such as those derived from Staphylococci species, Streptococci species (including Group A and B), Enterococci species; *Listeria*, *Bacillus* (including anthrax), *Corynebacteria*, *Neisseria* (*meningitidis* and *gonorrheae*), *Moraxella*, *Haemophilus* (typeable and nontypeable), *Pseudomonas* (*aeruginosa* and others), *Salmonella* (*typhi* and non-*typhi*), *Shigella*, resistant gram-negative enteric bacteria (*Enterobacter*, *Citrobacter*, *Klebsiella*, *E. coli*, etc.), *Clostridium difficile* and other *Clostridia*, *Bacteroides* and other anaerobes, Chlamydiaceae species (*C. trachomatis* and *C. pneumoniae*), *Mycoplasma* and *Legionella* as well as the *Treponemes* (syphilis, leptospirosis), and *Borrelia*.

The immunogenic compositions of the present invention may also be combined with fusion protein-polysaccharide conjugates as described in WO 09/143413.

The amount of immunogen and adjuvant in the inventive compositions and the dosages administered are determined by techniques well known to those skilled in the medical or veterinary arts taking into consideration such factors as the particular antigen, the adjuvant (if present), the age, sex, weight, species and condition of the particular patient, and the route of administration.

For instance, dosages of particular whole-cell immunogens for suitable hosts in which an immunological response is desired, can be readily ascertained by those skilled in the art from this disclosure, as is the amount of any adjuvant typically administered therewith. Thus, the skilled artisan can readily determine the amount of antigen and optional adjuvant in compositions and to be administered in methods of the invention. Typically, an adjuvant is commonly used as 0.001 to 50 wt % solution in phosphate buffered saline, and the antigen is present on the order of micrograms to milligrams, such as about 0.0001 wt % to about 5 wt %.

Typically, however, the antigen is present in an amount on the order of micrograms to milligrams, such as 1 µg to 100 µg, inclusive, or about 10 µg; or about 0.001 wt % to about 20 wt %, inclusive.

For compositions to be administered to an animal or human, including the components thereof, and for any particular method of administration, it is preferred to determine possible toxicity, such as by determining the lethal dose (LD) and $LD_{50}$ in a suitable animal model e.g., rodent such as mouse; and the dosage of the composition(s), concentration of components therein and timing of administering the composition(s), that elicit a suitable immunological response, such as by titrations of sera and analysis thereof for antibodies or antigens, e.g., by ELISA and/or RFFIT analysis. Such determinations do not require undue experimentation from the knowledge of the skilled artisan, this disclosure and the documents cited herein. And, the time for sequential administrations can be ascertained without undue experimentation.

Examples of immunogenic compositions of the invention include liquid preparations for orifice, e.g., oral, nasal, anal, vaginal, peroral, intragastric, mucosal (e.g., perlingual, alveolar, gingival, olfactory or respiratory mucosa) etc., administration such as suspensions, syrups or elixirs; and, preparations for parenteral, subcutaneous, intradermal, intramuscular or intravenous administration (e.g., injectable administration), such as sterile suspensions or emulsions. Such compositions may be in admixture with a suitable carrier, diluent, or excipient such as sterile water, physiological saline, glucose or the like. The compositions can also be lyophilized. The compositions can contain auxiliary substances such as wetting or emulsifying agents, pH buffering agents, gelling or viscosity enhancing additives, preservatives, flavoring agents, colors, and the like, depending upon the route of administration and the preparation desired. Standard texts, such as Remington, SCIENCE & PRACTICE OF PHARMACY (latest edition) and U.S. Patent Pub. No. 2009/0098165, may be consulted to prepare suitable preparations, without undue experimentation.

Compositions of the invention, are conveniently provided as liquid preparations, e.g., isotonic aqueous solutions, suspensions, emulsions or viscous compositions which may be buffered to a selected pH. If nasal or respiratory (mucosal) administration is desired, compositions may be in a form and dispensed by a squeeze spray dispenser, pump dispenser or aerosol dispenser. Aerosols are usually under pressure by means of a hydrocarbon. Pump dispensers can preferably dispense a metered dose or, a dose having a particular particle size.

Compositions of the invention can contain pharmaceutically acceptable flavors and/or colors for rendering them more appealing, especially if they are administered orally. The viscous compositions may be in the form of gels, lotions, ointments, creams and the like and will typically contain a sufficient amount of a thickening agent so that the viscosity is from about 2500 to 6500 cps, although more viscous compositions, even up to 10,000 cps may be employed. Viscous compositions have a viscosity preferably of 2500 to 5000 cps, since above that range they become more difficult to administer.

Liquid preparations are normally easier to prepare than gels, other viscous compositions, and solid compositions. Additionally, liquid compositions are somewhat more convenient to administer, especially by injection or orally, to animals, children, particularly small children. Viscous compositions, on the other hand, can be formulated within the appropriate viscosity range to provide longer contact periods with mucosa, such as the lining of the stomach or nasal mucosa.

The choice of suitable carriers and other additives will depend on the exact route of administration and the nature of the particular dosage form, e.g., liquid dosage form (e.g., whether the composition is to be formulated into a solution, a suspension, gel or another liquid form), or solid dosage form (e.g., whether the composition is to be formulated into a pill, tablet, capsule, caplet, time release form or liquid-filled form).

Solutions, suspensions and gels, normally contain a major amount of water (preferably purified water) in addition to the antigen, lipoprotein and optional adjuvant. Minor amounts of other ingredients such as pH adjusters (e.g., a base such as NaOH), emulsifiers or dispersing agents, buffering agents, preservatives, wetting agents, jelling agents, (e.g., methylcellulose), colors and/or flavors may also be present. The compositions can be isotonic, i.e., it can have the same osmotic pressure as blood and lacrimal fluid.

The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions may be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount which will achieve the selected viscosity. Viscous compositions are normally prepared from solutions by the addition of such thickening agents.

A pharmaceutically acceptable preservative can be employed to increase the shelf-life of the compositions. Benzyl alcohol may be suitable, although a variety of preservatives including, for example, parabens, thimerosal, chlorobutanol, or benzalkonium chloride may also be employed. A suitable concentration of the preservative will be from 0.02% to 2% based on the total weight although there may be appreciable variation depending upon the agent selected.

Those skilled in the art will recognize that the components of the compositions must be selected to be chemically inert with respect to the WCA and optional adjuvant. This will present no problem to those skilled in chemical and pharmaceutical principles, or problems can be readily avoided by reference to standard texts or by simple experiments (not involving undue experimentation), from this disclosure and the documents cited herein.

The immunologically effective compositions of this invention are prepared by mixing the ingredients following generally accepted procedures. For example the selected components may be simply mixed in a blender, or other standard device to produce a concentrated mixture which may then be adjusted to the final concentration and viscosity by the addition of water or thickening agent and possibly a buffer to control pH or an additional solute to control tonicity. Generally the pH may be from about pH 3 to pH 7.5. Compositions can be administered in dosages and by techniques well known to those skilled in the medical and veterinary arts taking into consideration such factors as the age, sex, weight, and condition of the particular patient or animal, and the composition form used for administration. Dosages for humans or other mammals can be determined without undue experimentation by the skilled artisan, from this disclosure, the documents cited herein, the Examples below (e.g., from the Examples involving mice and rabbits from the applications cited herein, especially because WCA can be administered in a manner and dose analogous to known vaccines.

Suitable regimes for initial administration and booster doses or for sequential administrations also are variable, may include an initial administration followed by subsequent administrations; but nonetheless, may be ascertained by the skilled artisan, from this disclosure, the documents cited herein, including applications cited herein, and the Examples below. The compositions can be administered alone, or can be co-administered or sequentially administered with other compositions of the invention or with other prophylactic or therapeutic compositions.

A vaccine of the present invention could be administered once, or twice or three times with an interval of 2 to 6 months between doses. Alternatively, a vaccine of the present invention, comprising could be administered as often as needed to an animal or a human being.

As used herein, "immunogenic composition" refers to a composition used to stimulate the immune system of a subject, so that one or more functions of the immune system are increased and directed towards the immunogenic composition. An antigen or immunogen is intended to mean a molecule containing one or more epitopes that can stimulate a host immune system to make a secretory, humoral and/or cellular immune response specific to that antigen. Immunogenic compositions can be used in the production of antibodies, both isolated polyclonal antibodies and monoclonal antibodies, using techniques known in the art. Immunogenic compositions include vaccines.

As used herein, "vaccine" refers to an agent used to stimulate the immune system of a subject so that protection is provided against an antigen not recognized as a self-antigen by the subject's immune system. Immunization refers to the process of inducing a high level of antibody and/or cellular immune response in a subject, that is directed against a pathogen or antigen to which the organism has been exposed. Vaccines and immunogenic agents as used herein, refer to a subject's immune system: the anatomical features and mechanisms by which a subject produces antibodies and/or cellular immune responses against an antigenic material that invades the subject's cells or extracellular fluids. In the case of antibody production, the antibody so produced can belong to any of the immunological classes, such as immunoglobulins, A, D, E, G, or M. Vaccines that stimulate production of immunoglobulin A (IgA) are of interest, because IgA is the principal immunoglobulin of the secretory system in warm-blooded animals. Vaccines are likely to produce a broad range of other immune responses in addition to IgA formation, for example cellular and humoral immunity. Immune responses to antigens are well-studied and reported widely. See, e.g., Elgert, IMMUNOL. (Wiley Liss, Inc., 1996); Stites et al., BASIC & CLIN. IMMUNOL., (7th Ed., Appleton & Lange, 1991).

As noted herein, adjuvants in immunology are often used to modify or augment the effects of a vaccine by stimulating the immune system to respond to the vaccine more vigorously, and thus providing increased immunity to a particular disease. Adjuvants accomplish this task by mimicking specific sets of evolutionarily conserved molecules, so called PAMPs, which include liposomes, lipopolysaccharide (LPS), molecular cages for antigen, components of bacterial cell walls, and endocytosed nucleic acids such as double-stranded RNA (dsRNA), single-stranded DNA (ssDNA), and unmethylated CpG dinucleotide-containing DNA. Because immune systems have evolved to recognize these specific antigenic moieties, the presence of an adjuvant in conjunction with the vaccine can greatly increase the innate immune response to the antigen by augmenting the activities of dendritic cells (DCs), lymphocytes, and macrophages by mimicking a natural infection. Furthermore, because adjuvants are attenuated beyond any function of virulence, they typically pose little or no independent threat to a host organism.

Typical inorganic adjuvants (sometimes referred to as "alum") include aluminum phosphate, aluminum hydroxide, and other phosphates. Although aluminum salts are popularly used in human vaccines, organic compounds, such as Squalene, are also used, more commonly in animal vaccines. Oil-based adjuvants are commonly used in some veterinary vaccines. Toxoids, such as tetanus toxoids, are also useful adjuvants in addition to the adjuvants described herein. Other proteinaceous adjuvants that may be used with the whole-cell immunogenic compositions of the present invention include duck hepatitis surface antigen (see U.S. Pat. No. 7,279,555) and bacterial porins (see U.S. Pat. No. 6,153,406; U.S. Pat. No. 6,013,267).

Particular embodiments of the invention provide for methods of preparing a whole-cell immunogenic composition comprising (a) growing pneumococci in culture medium (e.g., animal-product-free medium such as a soy-based medium); (b) washing and concentrating the pneumococci (e.g., to an $A_{600}$ of 32); (c) killing the pneumococci by selectively disrupting the cells by stirring at about 4° C. with chloroform (about 1/4 to 1/40 [vol/vol], inclusive) for a sufficient period of time (e.g., about 2 hours); or by stirring at about 4° C. with trichloroethylene (about 1/4 to 1/40 [vol/vol], inclusive) for a sufficient period of time (e.g., about 2 hours); or by stirring at about 4° C. with beta-propiolactone (about 1/4 to 1/4,000 [vol/vol], inclusive) for a sufficient period of time (e.g., about 24 hours); wherein the killed-cell preparations are not washed further; and (d) lyophilizing the chloroform- or trichloroethylene-killed cells to remove the chloroform or trichloroethylene; or incubating the beta-propiolactone-killed cells for 2 hours at 37° C. to decompose the beta-propiolactone and then lyophilizing the preparation.

The invention shall be further described by way of the following Examples, provided for illustration and not to be considered a limitation of the invention.

EXAMPLES

Example 1. Antigen Preparations

Strain Rx1E, in which the pneumolysin gene was replaced by a detoxified mutant PdT, was provided to us by James Paton (University of Adelaide, Australia). The entire lytA genomic coding region was replaced by the Janus cassette marked with kanamycin resistance gene rpsL, using the strategy described earlier. Sung et al., Appl. Environ. Microbio. 139 (2006); van Ginkel et al., 165 J. Immunol. 4778 (2000). Briefly, three PCR amplification products were created: (i) a 1-kb fragment upstream of the genomic region of lytA amplified with primers LAD1 (CAAGGTATC-CATCA TTCC) (SEQ ID NO:1) and LAD2 (CGCGGATC-CACAGTAGAGCCAGATGGC (SEQ ID NO: 2); BamHI site underlined), (ii) an 800-bp fragment downstream of lytA amplified with primers LAD3 (TTTGGGCCCGTTG-CACGCCGACTTGAGG (SEQ ID NO: 3); ApaI site underlined) and LAD4 (CTTTGCTTCTCAGAATCTAGG) (SEQ ID NO: 4), and (iii) the Janus cassette amplified with primers DAM351 (with ApaI site) and DAM406 (with BamHI site). Sung et al., 2001. The amplification products were digested at the sites introduced by PCR using the cognate restriction enzymes, gel purified, and then ligated overnight at 4° C. The ligation mixture was then used as a template for a final PCR using the outside primers LAD5 (CATAGCTTTAT-GACTGATACC) (SEQ ID NO: 5) and LAD6 (AAGGTCT-TCGAATCGGCAGTCG) (SEQ ID NO: 6), yielding a 3.2-kb amplification product: a tripartite DNA molecule with the Janus cassette flanked by lytA upstream and downstream sequences. This molecule was then transformed into a kanamycin-sensitive and streptomycin-resistant strain of Rx1E (PdT) by selecting for kanamycin-resistant colonies wherein the wild-type lytA gene was now replaced by the lytA::Janus disruption fragment.

The putative integrants were confirmed genotypically by PCR using a Janus-specific internal primer and the LAD5 primer, in comparison with the wild-type parental strains: the lytA::Janus strain yields that Janus-specific PCR product, but the wild-type strain does not. The lytA::Janus transformants were confirmed phenotypically by assessing susceptibility to lysis in the presence of 5% sodium deoxycholate: wild-type strains lyse, and strains lacking lytA are resistant to lysis. The lytA::Janus transformant of the Rx1E PdT strain was named RM200.

Four different killed-cell preparations, in which inactivation was achieved with ethanol, chloroform, trichloroethylene, or beta-propiolactone (WCE, WCC, WCT, or WCB, respectively), have been used herein. Generally, strain RM200 was grown to an A600 of 1.0, at which the viable count was approximately $6 \times 10^8$ CFU/ml. Further steps were performed at 4° C. The cells were collected by centrifugation and washed twice with lactated Ringer's solution (LR) (102 mM NaCl, 28 mM $NaC_3H_5O_3$, 1.5 mM $CaCl_2$, and 4 mM KCl). For WCE preparations, cells were resuspended to an $A_{600}$ of 10 and ethanol was added to 70% (vol/vol) gradually within 15 min. The suspension was stirred for 55 min, and the cells were pelleted again, washed twice, resuspended to an $A_{600}$ of 32 in LR containing 10% sucrose, cultured to ascertain sterility, and lyophilized in single-use aliquots. For WCC and WCT preparations, washed cells in LR with 10% sucrose at an $A_{600}$ of 32 were mixed with chloroform or trichloroethylene (1/40 [vol/vol]) for 2 hr. For WCB, washed cells in LR with 10% sucrose were mixed with beta-propiolactone (BPL) (1/4,000 [vol/vol]) for 24 hr at 4° C. followed by a 2-hr incubation at 37° C. to inactivate BPL. For WCC and WCT, the killed cells were not washed but, rather, directly lyophilized (which eliminates residual organic solvent); WCB was similarly lyophilized after inactivation of BPL. Preparation of supernatants was done by vortexing the suspension for 1 min and then centrifuging at 16,000×g for 5 min. Protein concentration was determined using the Total Protein Kit with bovine serum albumin as a standard (Sigma). SDS-PAGE was performed with precast 4 to 12% Bis-Tris SDS gels (Invitrogen, Carlsbad, Calif.). The WCC suspension was sonicated with a probe sonicator for at least 2 min at the highest intensity to prepare the WCC lysates.

One day prior to immunization, vaccines were prepared as follows. Frozen aliquots were thawed or lyophilized vials were reconstituted with sterile water, diluted to the appropriate concentration, and mixed with Al(OH)3 at the indicated concentration in a 15 ml conical tube, which was then tumbled overnight at 4° C. to allow for adsorption.

Aluminum hydroxide (alum) (2% Alhydrogel) was from Brenntag North America (Reading, Pa.). Beta-propiolactone (BPL) was from Fisher (Rockford, Ill.), and saline was from B. Braun Medical Inc. (Bethlehem, Pa.). All other reagents were obtained from Sigma. Cholera toxin (CT) was from List Biological Laboratories (Campbell, Calif.). Mutated derivatives of E. coli heat-labile toxin LT—mLT (R192G) and dmLT (R192G/L21 1A)—were obtained as described previously. Dickenson & Clements, 63 Infect. Immun. 1617 (1995). LT, cotton gauze patches, and sandpaper for transcutaneous immunization were provided by Intercell USA, Gaithersburg, Md.

Example 2. Immunization and Challenge of Mice

C57BL/6J mice (Jackson Laboratories, Bar Harbor, Me.) were used in all the experiments. The age at time of first immunization was between 4 and 6 weeks. Intranasal (i.n.) immunization was done by instilling 10 μl of saline, adjuvant only, or adjuvant mixed with antigen as specified atraumatically into nonanesthetized mice, a procedure that places no immunogen into the lungs; secondary immunizations were given after 1 week. Oral or sublingual immunization was carried out by placing 30 μl of vaccine mixed with 1% NaHCO3 and 30% sucrose on the oral surface or 5 μl of vaccine in the same diluent under the tongue, respectively. Oral or sublingual immunizations were carried out three times weekly, whereas only two doses were given with intranasal immunizations.

WCC was used in the transcutaneous immunization (TCI) experiment. WCC was rehydrated in water with 0.1% Zwittergent 3-14 (Calbiochem, Gibbstown, N.J.) and 1% arginine (Sigma) and then sonicated to an average size of 100 nm (WCA100) or 20 nm (WCA20). Mice were anesthetized with 2-2-2 tribromoethanol (Avertin; Sigma) and then shaved on the dorsum with a clipper. The shaved skin was hydrated by gentle touch with wet gauze, and excess water was removed by patting with dry, sterile gauze. After gentle abrasion with sandpaper, the immunizing solution (in a volume of 20 μl) was pipetted onto the patch, which was applied to the shaved area and left on the skin for 18 hr. Immunization was carried out three times at 2-week intervals. Blood was drawn 2 weeks after the last immunization for all immunizations except in the case of intranasal immunization, in which blood was drawn 3 weeks later and assayed for IL-17A production after stimulation with WCA. Gently restrained, nonanesthetized mice received two or three subcutaneous injections of 200 μl of adjuvant with or without antigen in the lower part of the back at 2-week intervals. Blood was drawn 1 or 2 weeks after the last immunization, and assayed for antibody and for IL-17A production in vitro after stimulation with WCA.

Nasopharyngeal (NP) Colonization Model:

To determine susceptibility to NP colonization, i.n. challenge with live encapsulated pneumococci was done as described previously (Malley et al., 2001): Four weeks after the last immunization (or 2 weeks for mice immunized by TCI), mice were challenged with $10^7$ CFU of serotype 6B strain 603 in 10 μl of PBS applied as described. To determine NP colonization, an upper respiratory culture was done by instilling sterile saline retrograde through the transected trachea, collecting the first 6 drops (about 0.1 ml) from the nostrils, and plating neat or diluted samples on blood agar plates containing 2.5 μg gentamicin/ml. The figures show the numbers of CFU per nasal wash sample of individual mice; the geometric means (GM) are displayed as a horizontal bar. For ease of statistical analysis, a sterile sample was assigned half the lower limit of detection (1.6 CFU/nasal wash), or 0.8 CFU/nasal wash.

Aspiration-Sepsis Challenge Model:

Two weeks after the last immunization, mice were gently anesthetized with isoflurane, held supine, and given a 100 μl intranasal inoculation containing an inoculum of type 3 strain WU-2 or type 5 strain DBL5 (Dr. David Briles, Univ. Alabama, Birmingham, Ala.) using a model we have described before (Lu et al., 77 Infect. Immun. 2076 (2009)), but with the modification that mice were not intranasally exposed to pneumococcus 2 days prior to aspiration challenge. This model induces sepsis and death within 3-4 days in nonimmunized mice. Mice are monitored twice daily and sacrificed by $CO_2$ inhalation and terminal exsanguination when demonstrating signs of illness following which a blood culture is obtained; in all were injected intraperitoneally with either 500 μl saline or 300 μl plus 200 μl of heat inactivated (56° C. for 30 min) serum obtained from rabbits immunized with aluminum hydroxide with or without WCA as described below. All animal studies were approved by local animal ethics committees.

Statistical Analysis:

Antibody and IL-17A concentrations and NP colonization densities were compared by the Mann-Whitney U test using PRISM (version 4.0a, GraphPad Software, Inc.). Differences in survival were analyzed with the Kaplan-Meier test, using PRISM as well. For the toxicology study, all comparisons were made to the group receiving the alum adjuvant alone. Comparisons of body weight, food consumption, body temperature, hematology (except leukocyte counts) coagulation parameters, clinical chemistry values, and organ weights were performed by group pair-wise comparisons using either ANOVA or Welch's test, with appropriate adjustment for multiple comparisons. For leukocyte counts and urinalyses, due to lack of normality, data were log and rank transformed, respectively, and transformed data were analyzed as above. Erythema, eschar and edema formation were analyzed by Cochran Mantel Haenszel Test.

Example 3. Rabbit Immunization and Toxicology Studies

All rabbit immunizations were performed at MPI (Mattawan, Mich.). Female New Zealand White rabbits in groups of three were given 0.5 ml injections of saline, $Al(OH)_3$ alone (containing 0.6 mg of Al), $Al(OH)_3$-adsorbed WCB at doses of 50, 500 or 5000 Ag or a whole cell Diphtheria-Tetanus-Pertussis whole cell (DTwP) vaccine (clinical product from Institute Butantan) intramuscularly on day 1, 15, 29 and 43. Sera were obtained before each immunization and at a terminal bleed on day 45 and shipped frozen to Children's Hospital Boston for measurement of antibodies. Observations for morbidity, mortality, clinical signs, body temperature and food and water consumption were conducted on a regular basis for all animals. Dermal irritation scores were evaluated prior to each dose and daily for three consecutive days following each dose (with the exception of the last dose). Clinical pathology was performed at baseline, on day 2 and at termination. At study termination (two days post last dose), macroscopic examinations were performed, organ weights were recorded, and the injection sites were examined microscopically.

Example 4. Enzyme-Linked Immunosorbent Assay (ELISA)

Assays for murine antibodies to WCA were done in Immulon 2 HB 96-microwell plates (Thermo Scientific, Waltham, Mass.) coated with WCA 100 ps of protein per ml in PBS. Plates were blocked with 1% BSA in PBS. Antibody diluted in PBS-T was added and incubated at room temperature for 2 hr Plates were washed with PBS-T, and secondary HRP-conjugated antibody to mouse immunoglobulin G, G1 or G2 (all from Sigma) was added and incubated at room temperature for 1 hr. The plates were washed and developed with SureBlue TMB Microwell Peroxidase Substrate (KPL, Gaithersburg, Md.).

Example 5. Assay of IL-17A Production in Whole Blood Samples

Fifty μl of heparinized blood was added to 450 pd Dulbecco Modified Eagle Medium (DMEM) (BioWhittaker, Walkersville, Md.) containing 10% low-endotoxin defined fetal bovine serum (FBS) (Hyclone, Logan, Utah), and 10 μg/ml ciprofloxacin (Cellgro, Manassas, Va.). Except for the nonstimulated control, the cultures were incubated at 37° C. for 6 days with $10^7$ cells of pneumococcal WCA. Supernatants were collected following centrifugation and stored at −80° C. until analyzed by enzyme-linked immunosorbent assay (ELISA) for IL-17A concentration (R&D Systems, Minneapolis, Minn.).

Example 6. Surface Killing Assay

Neutrophil surface killing assays were performed as described previously. Lu et al., 2008; Weinberger et al., 2009. Briefly, type 6B strain 0603 (Malley et al., 2005) was grown to mid-log phase and frozen in THY/10% glycerol at −80° C. On the day of the experiment, bacteria were thawed and diluted to 100 CFU/gL in RPMI supplemented with 10% FBS and opsonized with normal rabbit serum or serum from rabbits that had been immunized three times with WCV as described above for 30 min at 37° C. In all cases, rabbit sera were heated for 30 min at 52° C. to inactivate complement.

Polymorphonuclear leukocytes (neutrophils) were purified from the peripheral blood of human volunteers using a Histopaque gradient (Sigma-Aldrich, St. Louis, Mo.) according to the manufacturers instructions and used immediately. Five μl of the opsonized bacterial suspension, diluted to contain 30 cfu, was spotted at room temperature on trypticase soy agar with 5% defibrinated sheep blood (TSA II) (BD) with 5 replicates per plate, and the fluid was allowed to absorb, requiring about 15 min. Ten microliters of neutrophils ($3 \times 10^6$ cells/mL; resulting in a bacterial: neutrophil ratio of approximately 1:60) were then overlaid, allowed to absorb, and incubated overnight at 37° C. with 5% $CO_2$. Controls included bacteria spotted in the absence of neutrophils or with neutrophils but no serum.

Example 7. Sepsis Model in WCB-Immunized Animals

Animals were immunized twice, 2 weeks apart, subcutaneously (s.q.), with alum and doses of WCB corresponding to 0, $10^7$ CFU or $10^8$ CFU before killing. Blood was sampled 6 days after the second dose for IL-17A and antibody measurement. Mice were challenged 2 days later (no prior exposure) to WU-2 aspiration, and monitored for illness and death twice a day for 7 days. Final blood was obtained from survivors on day 7 (blood culture). Results are shown in the Figures.

Figure 9A:
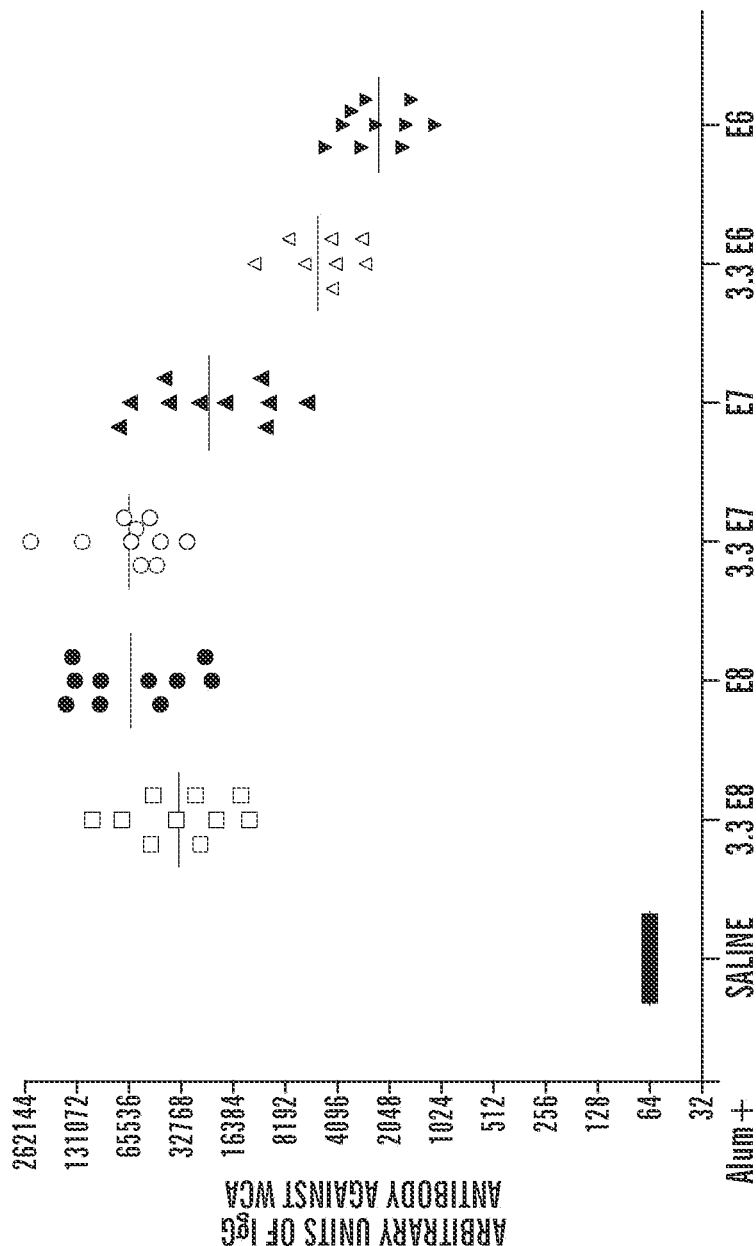
FIGS. 9A-9B show detailed dose-responses of mice to Al(OH)3-adsorbed WCB given thrice by subcutaneous injection.
Figure 9B:
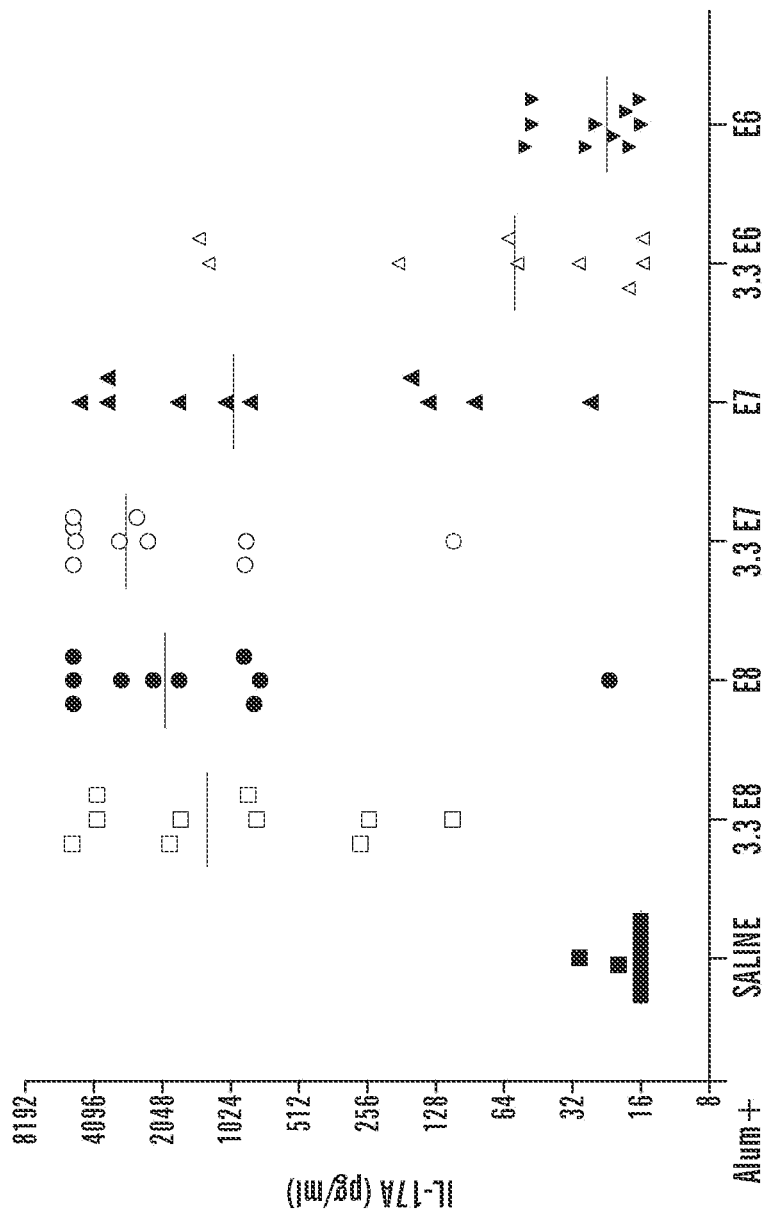

This experiment was repeated using different doses of WCB, and the results are shown in FIGS. 2B, 9A and 9B. In this sepsis challenge, all the mice immunized with $10^7$ to $3 \times 10^8$ CFU survived challenge; and there were three deaths in the $3 \times 10^6$ and $10^6$ groups.

Example 8. Assessing Buccal/Sublingual/Subcutaneous Immunization with WCC

In this example, "oral" or "buccal" route of administration used WCA and adjuvant in 30 l volume placed in awake mouse under the tongue. Diluent for vaccine consists of 30% sucrose, LR and sodium bicarbonate. The "sublingual" route of administration used WCA and adjuvant in a 5-μl volume placed under the tongue, with the same diluent. The "subcutaneous" route was diluent in LR only. The oral route appears effective, based on experiments. This study aimed to compare the efficacy of oral vs. more concentrated sublingual administration vs. subcutaneous administration of WCA with dmLT, and evaluate the immunogenicity and protective capacity. Immunogens were prepared with dmLT: weight 27 mg from 90 mg total, dissolved in 50 μl 3% sodium bicarbonate/30% sucrose LR buffer to make final 10 mg/ml. This formula was prepared for a single immunization only, and made fresh for second immunization. WCC was lyophilized in LR, and reconstituted in 80 μl 3% NaHCO$_3$ and 30% sucrose to get 5 E10; or 400 μl to get E10. Groups and routes are shown in Table 1.

TABLE 1

Routes and composition of vaccine

| Group | #M | times | Interval (weeks) | 3% NaHCO$_3$ and 30% sucrose | Vaccine (5E10) | E10 | DmLT | Total |
|---|---|---|---|---|---|---|---|---|
| 1 dmLT/oral | 20 | 2 | 1 | 638 | 0 | 0 | 22 | 660 |
| 2 DmlT + E9/oral | 20 | 2 | 1 | 198 | 440 | 0 | 22 | 660 |
| 3 DmLT + 2E8/oral | 10 | 2 | 1 | 99 | 0 | 220 | 11 | 660 |
| 4 DmLT/sublingual | 10 | 2 | 1 | 48 | 0 |  | 12 | 60 |
| 5 DmlT + 2E8/sublingual | 10 | 3 | 1 | 0 | 48 |  | 12 | 60 |
| 6 DmLT + 4E7/sublingual | 10 | 3 | 1 | 0 | 0 | 48 | 12 | 60 |
| 7 DmLT/subcu | 10 | 3 | 2 | LR2389 | 0 | 0 | 12 | 2400 |
| 8 DmLT + E9/subcu | 10 | 3 | 2 | LR1189 | 0 | 1200 | 12 | 2400 |

TABLE 2

Groups and doses

| Cage | Immunogen | times | Interval (weeks) | Mice | Challenge |
|---|---|---|---|---|---|
| 1 | dmLT/oral | 3 | 1 | 5 | 603 |
| 2 |  |  |  | 5 |  |
| 3 | dmLT/oral | 3 | 1 | 5 |  |
| 4 |  |  |  | 5 |  |
| 5 | dmlT + E9/oral | 3 | 1 | 5 |  |
| 6 |  |  |  | 5 |  |
| 7 | dmlT + E9/oral | 3 | 1 | 5 |  |
| 8 |  |  |  | 5 |  |
| 9 | dmLT + 2E8/oral | 3 | 1 | 5 |  |
| 10 |  |  |  | 5 |  |

TABLE 2-continued

Groups and doses

| Cage | Immunogen | times | Interval (weeks) | Mice | Challenge |
|---|---|---|---|---|---|
| 11 | dmLT/sublingual | 3 | 1 | 5 |  |
| 12 |  |  |  | 5 |  |
| 13 | dmLT + 2E8/sublingual | 3 | 2 | 5 |  |
| 14 |  |  |  | 5 |  |
| 15 | dmLT + 4E7/sublingual | 3 | 2 | 5 |  |
| 16 |  |  |  | 5 |  |
| 17 | dmLT/subcu | 2 | 2 | 5 |  |
| 18 |  |  |  | 5 |  |
| 19 | dmLT + E9/subcu | 2 | 2 | 5 |  |
| 20 |  |  |  | 5 |  |
| Total |  |  |  | 100 |  |

Figure 11B:
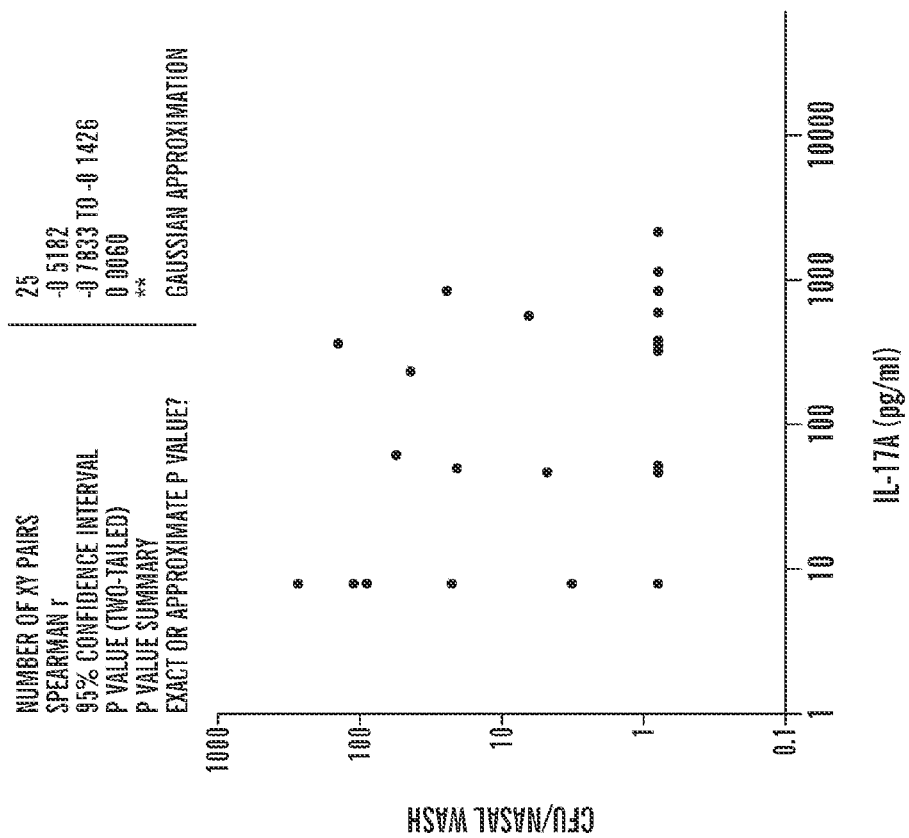
FIG. 11B shows correlation between IL-17A production and colonization.
Figure 11C:
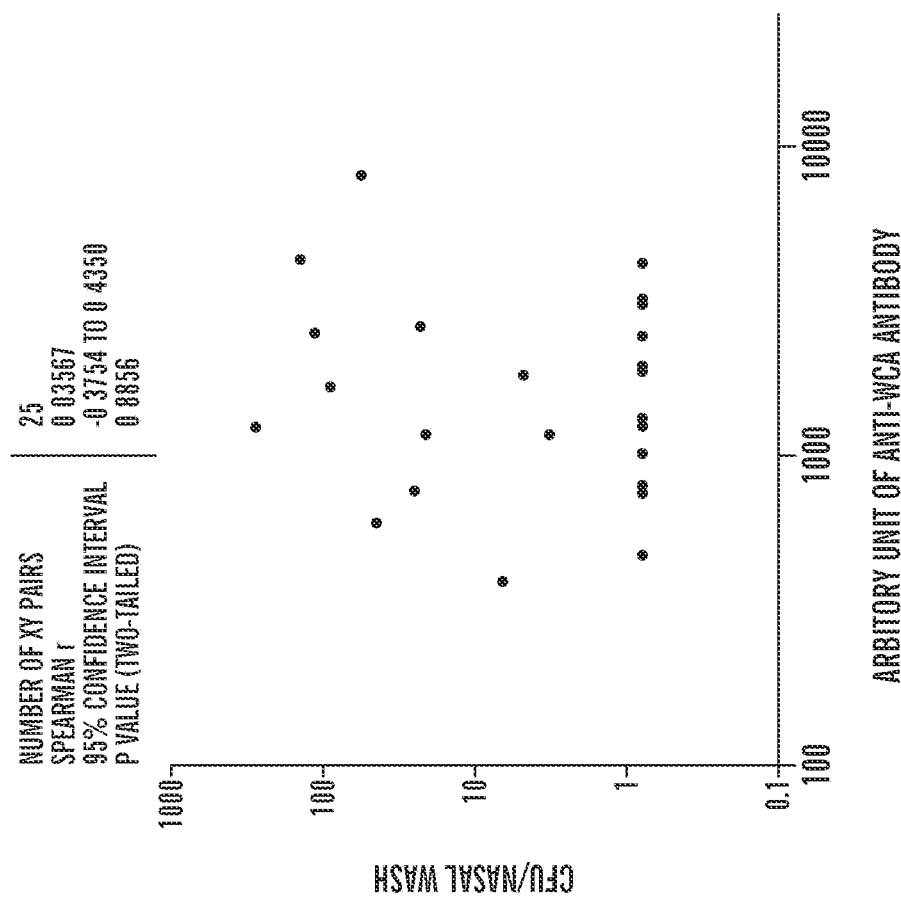
FIG. 11C shows correlation between serotype responses and colonization.

All mice were immunized on day 1, cages 1 to 16 on day 8, all cages on day 15. Blood was drawn on day 34, challenge on day 42, and sacrifice on day 58. Cages 17 and 18 were withdrawn from the experiment. The immunogenicity results are shown in FIGS. 10A-10B; and colonization results are shown in FIGS. 11A-11C. Oral immunization was effective; and sublingual immunization was not significantly different from oral. The correlation between cytokine production and CFU was fairly consistent. The subcutaneous route was effective in generating antibody, as shown in the figures.

Example 9. Assessing Subcutaneous Vaccination

As discussed in Example 1, WCC was resuspended in 400 ul water for s.q. immunization. The preparation was made fresh for second immunization. WCC E8 (37 lm) was WCC E8 mixed with alum overnight at 4° C. then kept at 374° C. for 1 month. WCB, resuspended in 1.3 ml water to match OD with WCC. WCB lots were kept in cold room for 5 weeks then lyophilized. Resuspended in 400 μl water. Immunization was performed three times with two week intervals.

TABLE 3

WCC and Al(OH)3 (alum) vaccine preparations

| Oral Group | # M | Volume dilute | Vaccine | Alum | Total |
|---|---|---|---|---|---|
| 1 Alum | 10 | 2250 | 0 | 250 | 2500 |
| 2 WCC E8 + Alum | 10 | 2125 | 125 | 250 | 2500 |
| 3 WCC E7 + Alum | 10 | 2237.5 | 12.5 | 250 | 2500 |

TABLE 3-continued

WCC and Al(OH)3 (alum) vaccine preparations

| Oral Group | # M | Volume dilute | Vaccine | Alum | Total |
|---|---|---|---|---|---|
| 4 WCC E6 + Alum | 10 | 2249 | 1.25 | 250 | 2500 |
| 5 WCC E8 | 10 | 2375 | 125 | 0 | 2500 |
| 6 WCC E7 | 10 | 2487.5 | 12.5 | 0 | 2500 |
| 7 WCC E6 | 10 | 2499 | 1.25 | 0 | 2500 |
| 8 WCC E8 (371m) + Alum | 10 | 2125 | 125 | 250 | 2500 |
| 9 WCB-but E8 + Alum | 10 | 2125 | 125 | 250 | 2500 |
| 10 WCB lot 4 E8 + Alum | 10 | 2125 | 125 | 250 | 2500 |

TABLE 4

Immunization groups

| Cage | Immunogen | Mice | Challenge |
|---|---|---|---|
| 1 | Alum | 5 | 603 |
| 2 | | 5 | |
| 3 | WCC E8 + Alum | 5 | |
| 4 | | 5 | |
| 5 | WCC E7 + Alum | 5 | |
| 6 | | 5 | |
| 7 | WCC E6 + Alum | 5 | |
| 8 | | 5 | |
| 9 | WCC E8 | 5 | |
| 10 | | 5 | |
| 11 | WCC E7 | 5 | |
| 12 | | 5 | |
| 13 | WCC E6 | 5 | |
| 14 | | 5 | |
| 15 | WCC E8 (37 1m) + Alum | 5 | |
| 16 | | 5 | |
| 17 | WCB-but E8 + Alum | 5 | |
| 18 | | 5 | |
| 19 | WCB lot 4 E8 + Alum | 5 | |
| 20 | Alum | 5 | |
| Total | | 100 | |

Mice were immunized on days 1, 16, and 30. Eye bleeds were conducted on day 30 and 50. On day 55, mice were challenged with $10^7$ CFU of Pn strain (0603). On day 65, the mice were euthanized by $CO_2$ and nasal washes collected. Results are shown in the Figures.

Example 10. Transcutaneous Administration Study

For a transdermal study, immunogens were prepared as follows: WCC, resuspended in 400 μl water for immunization (made fresh for second immunization). WCC, resuspended in 800 μl ZWR (0.1% zwittergen 3-14 and 1% Arg). The WCC suspension was sonicated with a probe sonicator for at least 2 min at the highest intensity to prepare the WCC lysates. For example, using intensity 4, sonicate two tubes WCC in 2 ml conical tube for six times 5 sec with 10 sec swirl to make "WCA 100". Sonicate twenty-four times, 5 sec each, to make WCA. "WCA/bust" is WCC resuspended in water and combine two tubes in 2 ml tube. Using intensity 4, sonicate six times for 20 sec with 10 sec interval.

TABLE 5

Route and dose preparation

| Route | Group | #M | times | diluent | Volume diluent | Vaccine | LT/Alum | Total |
|---|---|---|---|---|---|---|---|---|
| TCI | 1 LT only | 10 | 3 | ZWR | 250 | 0 | 28 | 278 |
| TCI | 2 WCA 100 only | 10 | 3 | ZWR | 28 | 250 | 0 | 250 |
| TCI | 3 WCA 100 + LT | 10 | 3 | ZWR | 0 | 250 | 28 | 278 |
| TCI | 4 WCA 20 + LT | 10 | 3 | ZWR | 0 | 250 | 28 | 278 |
| in | 5 LT only | 10 | 2 | saline | 220 | 0 | 2.5 | 222.5 |
| in | 6 WCA + LT | 10 | 2 | saline | 110 | 110 | 2.5 | 222.5 |
| in | 7 WCA/bust + LT | 10 | 2 | LR | 0 | 220 | 2.5 | 222.5 |

Fragments with a mean diameter of 100 or 20 nm in dosage equivalent to $10^8$ cells were applied, along with 1 μg of LT adjuvant where indicated, 20 μl in cotton gauze patches onto dorsal skin gently abraded to remove the stratum corneum. The patch was left in place for 18 hr. This immunization was given thrice with a 2-week interval. Blood samples were taken 10 days after the third immunization for assays of IL-17A, and pneumococcal challenge was done 6 days later. Immunogenicity and colonization data are presented in FIGS. 12A-12D.

Example 11. WCA in Al(OH)3 (alum)

Groups of animals were immunized subcutaneously with WCA in alum as follows:

TABLE 6

WCA vaccination groups.

| Group | #M | times | diluent | Volume diluent | Vaccine | LT/Alum | Total |
|---|---|---|---|---|---|---|---|
| 1 Alum | 10 | 3 | saline | 2250 | 0 | 250 | 2500 |
| 2 E8 + Alum | 10 | 3 | saline | 2125 | 125 | 250 | 2500 |
| 3 E9 + Alum | 10 | 3 | saline | 1000 | 1250 | 250 | 2500 |

Example 13. BPL-Killed Vaccine

To evaluate BPL (beta-propiolactone)-mediated killing of *Streptococcus pneumoniae* for the preparation of whole cell antigen (called WCB in this report), the killing effect of BPL for the preparation of WCB and a wide range of BPL concentrations were used (0.025%, 0.1%, 0.2%, 0.4%, 0.6%, 0.8%, 1%). Subsequent studies used 0.025% (1:4000) BPL concentration with overnight incubation at 4° C. followed by inactivation at 37° C. for 2 hr. In all cases, 100% killing was observed.

More specifically, vaccine preparations were used (WCB):
- (A) WCB provided by Butantan Institute, Brazil (OD 38.6, in LR+0.2% glucose, 0.025% BPL, 4° C. O/N with 2 hr inactivation at 37° C., lyophilized);
- (B) WCB prepared as herein (WCB vaccine, OD 32, in LR+0.2% glucose, 0.025% BPL, 4° C. 0/N with 2 hr inactivation at 37° C., lyophilized);
- (C) WCB 3-wk-old kept in cold (WCB OD32, in LR+10% sucrose, 0.025% BPL, 4° C. 0/N with 2 hr inactivation at 37° C., not lyophilized); and
- (D) WCC (chloroform killed; 1:40 chloroform, lyophilized). The vaccine preparations were compared by Gram staining.

The IL-17A secretion by splenocytes was measured using cellular suspensions of splenocytes were obtained by passing spleens from mice through a 70-mm cell strainer. After washing and removal of red blood cells by hemolysis, cells were plated into 24-well tissue culture plates at a concentration of $5 \times 10^6$ cells/well in 500 µl of DMEM/F12 with L-glutamine supplemented with 10% fetal calf-serum, 50 µM 2-mercaptoethanol (Sigma), and 10 µg/ml ciprofloxacin. Following 90-hour (previously, cells were harvested after 72 hours only) stimulation with all WCB (equivalent to $10^7$ cfu/ml) and their supernatants were collected following centrifugation and analyzed by ELISA for IL-17A concentration (R&D Systems, Minneapolis, Minn.). Supernatants were analyzed and read against a standard.

OD was measured for all in spectrophotometer. Protein quantification was done by BCA method. Briefly, 100 µl of each was mixed with 1 mL of BCA working reagent and incubated for 30 min at 60° C. and values were determined against the standard. For SDS-PAGE, supernatant was run from each preparation on 4-12% Bis-Tris gel to check the protein. For supernatant, lyophilized vaccines were reconstituted in dH$_2$O and centrifuged at 8,000 RPM for 10 min and supernatant collected. Based on OD readings, the Butantan vaccine was diluted to final OD32 (1.3:1 dilution).

Stimulation of Splenocytes from Mice Exposed to Pneumococci:

Priming for IL-17A production was assayed in vitro in spleen cells, incubated for more than 90 hrs with WCB. IL-17A stimulation was done for Butantan vaccine with dilutions (1.3:1 dilutions) IL-17A expression measured. Results are shown in Table 9:

TABLE 7

Comparison of BPL preparations

Gram Staining

| Sample | Result |
|---|---|
| A | GN > GP (>70% GN) |
| B | GN > GP (>70% GN) |
| C | All GN |
| D | GN > GP (>70% GN) |

TABLE 7-continued

Comparison of BPL preparations

OD Measurements

| Sample | OD$_{600}$ before Lypholization | OD$_{600}$ after Lypholization |
|---|---|---|
| A | 43.5 | 24.9 |
| B | 32 | 19 |
| C | 32 | 20 |
| D | 32 | 23.5 |

Protein Content

| Sample | Whole cell (µg/µl) | Supernatant (µg/µl) |
|---|---|---|
| A | 9 | 3 |
| B | 9 | 1.84 |
| C | 4.95 | 1.79 |
| D | 4.33 | 1.64 |

(GN = Gram-negative; GP = gram-positive)

Figure 14:
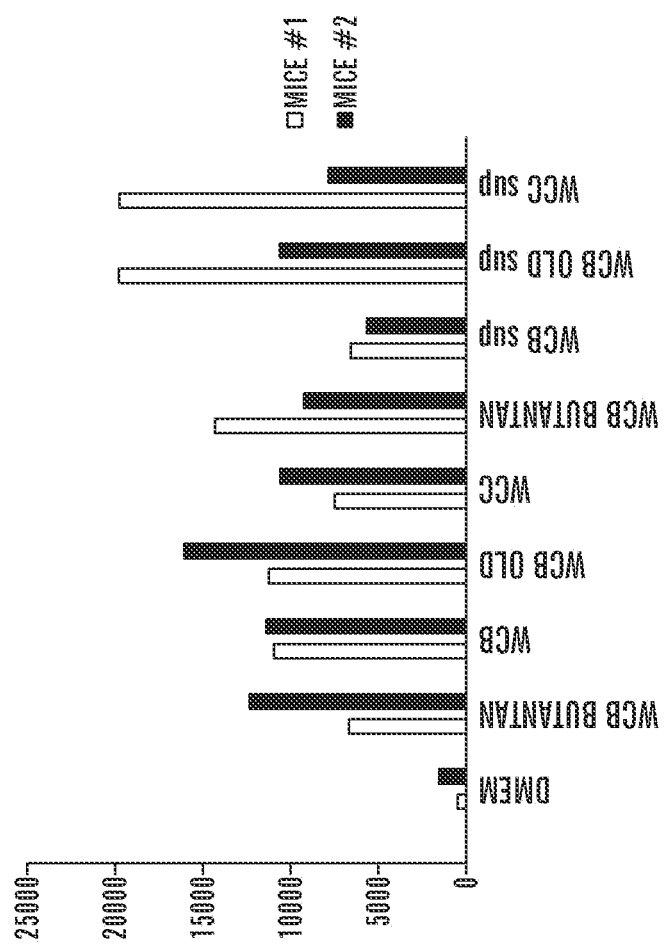
FIG. 14 shows IL-17A stimulation data, in which "sup" denotes the stimulation by supernatant collected after centrifugation from WCB.

Supernatants of each preparation were collected after centrifugation, for lyophilized after re-suspension in 400 µl of dH$_2$O while for non-lyophilized just 400 µl of vaccine preparation. Aliquots of 10 µl each were run on 4%-12% Bis Tris gels SDS-PAGE gels, which revealed a much greater concentration of comparable proteins in the WCC supernatant than in the other preparations (consistent with greater protein recovery compared to ethanol-killed cells as shown in FIGS. 3A-3B). IL-17A stimulation data is shown in FIG. 14, in which "sup" denotes the stimulation by supernatant collected after centrifugation from WCB.

The invention claimed is:

1. A method for producing a killed, whole-bacterial immunogenic composition from *Streptococcus pneumoniae* which elicits an antibody-mediated immune response and a T-lymphocyte mediated immune response, comprising
   (i) selectively disrupting the *Streptococcus pneumoniae* bacteria in a bacterial preparation into a soluble fraction and an insoluble fraction using a solvent that is at least one of: an immiscible solvent, a volatile agent which evaporates at room temperature, or beta-propiolactone whereby the solvent maintains the overall structure of the *Streptococcus pneumoniae* bacterial cell,
   (ii) removing the solvent by evaporation, hydrolysis or lyophilization or heat inactivation at 37° C. such that the soluble fraction is not removed from the bacterial preparation and both the soluble and cellular fraction remain in the immunogenic composition and wherein the bacterial cell preparation is not washed;
   (iii) resuspending the bacterial preparation in an aqueous solution comprising an adjuvant, wherein the soluble fraction elicits an antibody-mediated immune response, and the cellular fraction elicits a T-lymphocyte mediated immune response.

2. The method according to claim 1, wherein said soluble fraction induces a serotype-independent antibody response, and said cellular fraction induces increased phagocytosis.

3. The method according to claim 1, wherein the immiscible solvent or volatile agent which evaporates at room temperature is chloroform or trichloroethylene.

4. The method according to claim 1, wherein the adjuvant is Al(OH)$_3$ or aluminum phosphate.

* * * * *